(12) United States Patent
Nagel

(10) Patent No.: US 11,090,482 B2
(45) Date of Patent: Aug. 17, 2021

(54) METHOD AND DEVICES FOR TREATING MUSCLES

(71) Applicant: Vomaris Innovations, Inc., Tempe, AZ (US)

(72) Inventor: Michael Nagel, Tempe, AZ (US)

(73) Assignee: Vomaris Innovations, Inc., Tempe, AZ (US)

( * ) Notice: Subject to any disclaimer, the term of this patent is extended or adjusted under 35 U.S.C. 154(b) by 53 days.

(21) Appl. No.: 15/578,661

(22) PCT Filed: Jun. 2, 2016

(86) PCT No.: PCT/US2016/035540
§ 371 (c)(1),
(2) Date: Nov. 30, 2017

(87) PCT Pub. No.: WO2016/196809
PCT Pub. Date: Dec. 8, 2016

(65) Prior Publication Data
US 2018/0147404 A1    May 31, 2018

Related U.S. Application Data

(60) Provisional application No. 62/327,207, filed on Apr. 25, 2016, provisional application No. 62/327,202, (Continued)

(51) Int. Cl.
*A61N 1/04* (2006.01)
*A61N 1/36* (2006.01)

(52) U.S. Cl.
CPC ......... *A61N 1/0484* (2013.01); *A61N 1/0452* (2013.01); *A61N 1/0456* (2013.01); *A61N 1/36003* (2013.01); *A61N 1/36042* (2013.01)

(58) Field of Classification Search
CPC .. A61N 1/0484; A61N 1/0452; A61N 1/0456; A61N 1/0476; A61N 1/0492;
(Continued)

(56) References Cited

U.S. PATENT DOCUMENTS

| 7,457,667 | B2 * | 11/2008 | Skiba | A61N 1/303 600/372 |
| 2005/0004508 | A1 * | 1/2005 | Sun | A61N 1/0428 604/20 |

(Continued)

FOREIGN PATENT DOCUMENTS

| WO | 2014/178943 A1 | 11/2014 |
| WO | 2016/196809 A1 | 12/2016 |
| WO | 2017/189366 A1 | 11/2017 |

OTHER PUBLICATIONS

International Search Report and Written Opinion dated Jul. 7, 2017 for International Application Serial No. PCT/US17/28943.

(Continued)

*Primary Examiner* — George R Evanisko
(74) *Attorney, Agent, or Firm* — K&L Gates LLP; Louis C. Cullman; Hal Gibson

(57) ABSTRACT

An apparatus includes multiple first reservoirs and multiple second reservoirs joined with a substrate. Selected ones of the multiple first reservoirs include a reducing agent, and first reservoir surfaces of selected ones of the multiple first reservoirs are proximate to a first substrate surface. Selected ones of the multiple second reservoirs include an oxidizing agent, and second reservoir surfaces of selected ones of the multiple second reservoirs are proximate to the first substrate surface.

7 Claims, 9 Drawing Sheets

Related U.S. Application Data filed on Apr. 25, 2016, provisional application No. 62/170,275, filed on Jun. 3, 2015.

(58) Field of Classification Search
CPC ...... A61N 1/0496; A61N 1/24; A61N 1/3785; A61N 1/326; A61N 1/20; A61N 1/205
See application file for complete search history.

(56) References Cited

U.S. PATENT DOCUMENTS

| | | | |
|---|---|---|---|
| 2005/0244484 A1* | 11/2005 | Flick | A61F 13/00034 |
| | | | 424/445 |
| 2007/0088341 A1* | 4/2007 | Skiba | A43B 1/0045 |
| | | | 606/2 |
| 2007/0239212 A1 | 10/2007 | Schneider et al. | |
| 2009/0112283 A1* | 4/2009 | Kriksunov | A61N 1/205 |
| | | | 607/46 |
| 2009/0209830 A1* | 8/2009 | Nagle | A43B 7/147 |
| | | | 600/301 |
| 2012/0172940 A1* | 7/2012 | Wahls | A41D 1/005 |
| | | | 607/3 |
| 2014/0213940 A1* | 7/2014 | Mayer | A61N 1/0484 |
| | | | 601/21 |
| 2018/0185639 A1* | 7/2018 | Nachum | A61N 1/36003 |
| 2019/0117955 A1 | 4/2019 | Nagel | |

OTHER PUBLICATIONS

International Search Report and Written Opinion dated Sep. 1, 2016 for International Application Serial No. PCT/US16/35540.

\* cited by examiner

METHOD AND DEVICES FOR TREATING MUSCLES

RELATED APPLICATIONS

This application is an application under 35 U.S.C. § 371 of International Patent Application PCT/US2016/035540 filed on Jun. 2, 2016, which claims the benefit of U.S. provisional patent application No. 62/170,275, filed Jun. 3, 2015, U.S. provisional patent application No. 62/327,202, filed Apr. 25, 2016, and U.S. provisional patent application No. 62/327,207, filed Apr. 25, 2016; the disclosures of each of which are incorporated herein by reference in their entirety.

FIELD

The present specification relates to bioelectric devices designed for use on certain areas of the body, for example on or around muscles or other contoured areas, and methods of manufacture and use thereof.

SUMMARY

Disclosed herein are systems, devices, and methods for use in treatment of subjects, in particular treatment of specific areas of tissue, for example around or about a muscle or muscle group, for example the deltoids, the triceps, the biceps, the quadriceps, the calf, the shoulder, the abdominals, the back, or the like. Disclosed embodiments can prevent muscle injury, reduce or repair muscle damage (for example, such as can occur during a workout or athletic performance), improve muscle function, improve athletic performance, and accelerate muscle recovery, for example by activating enzymes, increasing glucose uptake, driving redox signaling, increasing $H_2O_2$ production, increasing cellular protein sulfhydryl levels, and increasing (IGF)-1 R phosphorylation. Embodiments can also up-regulate integrin production and accumulation in treatment areas.

In embodiments the systems, devices, and methods include fabrics, for example clothing or dressings, for example compression garments or clothing, that comprise one or more biocompatible electrodes configured to generate at least one of a low level electric field (LLEF) or low level electric current (LLEC). Embodiments disclosed herein can produce a uniform current or field density.

Certain embodiments can comprise a solution or formulation comprising an active agent and a solvent or carrier or vehicle.

DETAILED DESCRIPTION

Figure 1:
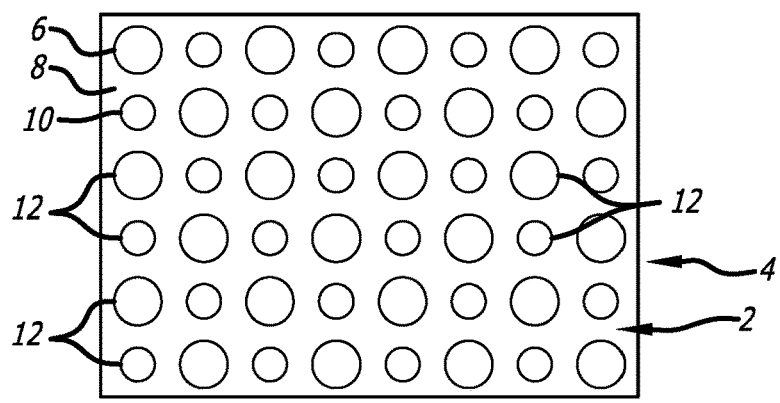
FIG. 1 is a detailed plan view of an embodiment disclosed herein.

Embodiments disclosed herein include systems and devices that can provide a low level electric field ("LLEF") to a tissue or organism (a "LLEF system") or, when brought into contact with an electrically conducting material, can provide a low level electric current ("LLEC") to a tissue or organism (a "LLEC system"). Thus, in embodiments a LLEC system is a LLEF system that is in contact with an electrically conducting material, for example a liquid material. In certain embodiments, the electric current or electric field can be modulated, for example, to alter the duration, size, shape, field depth, duration, current, polarity, or voltage of the system. For example, it can be desirable to employ an electric field of greater strength or depth to achieve optimal treatment. In embodiments the watt-density of the system can be modulated.

Embodiments disclosed herein include methods of treatment, for example treatment of a muscle or muscle group (for example a muscle group surrounding a joint), either before, during, or after athletic activity or exercise. For example, a method of treatment disclosed herein can comprise applying an embodiment disclosed herein to a muscle or muscle group, then stretching that muscle or muscle group, prior to exercise or athletic performance. Further methods of treatment disclosed herein can comprise application of an embodiment disclosed herein to a muscle or muscle group, then stretching that muscle or muscle group, after exercise or athletic performance. Further methods of treatment disclosed herein can comprise application of an embodiment disclosed herein to a muscle or muscle group while the subject sleeps.

Definitions

"Activation agent" as used herein means a composition useful for maintaining a moist and/or electrically conductive environment within and about the treatment area. Activation agents can be in the form of gels or liquids. Activation agents can be conductive. Activation gels can provide a temperature increase to an area where applied. Activation gels can also be antibacterial.

"Affixing" as used herein can mean contacting a patient or tissue with a device or system disclosed herein. In embodiments "affixing" can include the use of straps, elastic, etc.

"Antimicrobial agent" as used herein refers to an additional agent that kills or inhibits the growth of microorganisms. On type of antimicrobial agent can be an antibacterial agent. "Antibacterial agent" or "antibacterial" as used herein refers to an agent that interferes with the growth and reproduction of bacteria. Antibacterial agents are used to disinfect surfaces and eliminate potentially harmful bacteria. Unlike antibiotics, they are not used as medicines for humans or animals, but are found in products such as soaps, detergents, health and skincare products and household cleaners.

"Applied" or "apply" as used herein refers to contacting a surface with a conductive material, for example printing, painting, or spraying a conductive ink on a surface. Alternatively, "applying" can mean contacting a patient or tissue or organism with a device or system disclosed herein.

"Compression fabric" as used herein refers to a fabric that displays elastic properties. For example, compression fabrics can comprise lycra, or any suitable material.

"Conductive material" as used herein refers to an object or type of material which permits the flow of electric charges in one or more directions. Conductive materials can include solids such as metals or carbon, or liquids such as conductive metal solutions and conductive gels. Conductive materials can be applied to form at least one matrix. Conductive liquids can dry, cure, or harden after application to form a solid material.

"Discontinuous region" as used herein refers to a "void" in a material (for example a substrate) such as a hole, slot, or the like. The term can mean any void in the material though typically the void is of a regular shape. A void in the material can be entirely within the perimeter of a material or it can extend to the perimeter of a material.

"Dots" as used herein refers to discrete deposits of similar or dissimilar reservoirs that can function as at least one battery cell. The term can refer to a deposit of any suitable size or shape, such as squares, circles, triangles, lines, etc. The term can be used synonymously with, for example, microcells, electrodes, etc.

"Electrode" refers to similar or dissimilar conductive materials. In embodiments utilizing an external power source the electrodes can comprise similar conductive materials. In embodiments that do not use an external power source, the electrodes can comprise dissimilar conductive materials that can define an anode and a cathode. Electrodes or dots can be of similar or dissimilar shapes and sizes, whether or not they are made of the same material.

"Expandable" as used herein refers to the ability to stretch while retaining structural integrity and not tearing. The term can refer to solid regions as well as discontinuous or void regions; solid regions as well as void regions can stretch or expand.

"Matrix" or "matrices" as used herein refer to a pattern or patterns, such as those formed by electrodes or dots on a surface, such as a fabric or a fiber, or the like. Matrices can be designed to vary the electric field or electric current or microcurrent generated. For example, the strength and shape of the field or current or microcurrent can be altered, or the matrices can be designed to produce an electric field(s) or current or microcurrent of a desired strength or shape.

"Stretchable" as used herein refers to the ability of embodiments that stretch without losing their structural integrity. That is, embodiments can stretch to accommodate irregular skin surfaces or surfaces wherein one portion of the surface can move relative to another portion.

"Treatment" as used herein can include the use of disclosed embodiments on muscles or muscle groups.

LLEC/LLEF Systems, Devices, and Methods of Manufacture

In embodiments, devices disclosed herein comprise patterns of micro-batteries that create a field between each dot pair. In embodiments, the unique field is very short, e.g. in the range of physiologic electric fields. In embodiments, the direction of the electric field produced by disclosed devices is omnidirectional over the treatment area.

Embodiments of the LLEC or LLEF systems and devices disclosed herein can comprise electrodes or microcells or reservoirs. Each electrode or microcell or reservoir can comprise a conductive metal. In embodiments, the electrodes or microcells can comprise any electrically-conductive material, for example, electrically conductive hydrogels, metals, electrolytes, superconductors, semiconductors, plasmas, and nonmetallic conductors such as graphite and conductive polymers. Electrically conductive metals can include, for example, silver, copper, gold, aluminum, molybdenum, zinc, lithium, tungsten, brass, carbon, nickel, iron, palladium, platinum, tin, bronze, carbon steel, lead, titanium, stainless steel, mercury, Fe/Cr alloys, and the like. The electrode can be coated or plated with a different metal such as aluminum, gold, platinum or silver.

Dissimilar metals used to make a LLEC or LLEF system disclosed herein can be silver and zinc, and the electrolytic solution can include sodium chloride in water. In certain embodiments the electrodes are applied onto a non-conductive surface to create a pattern, most preferably an array or multi-array of voltaic cells that do not spontaneously react until they contact an electrolytic solution. Sections of this description use the terms "printing" with "ink," but it is to be understood that the patterns may also be "painted" with "paints." The use of any suitable means for applying a conductive material is contemplated. In embodiments "ink" or "paint" can comprise any material such as a solution suitable for forming an electrode on a surface such as a conductive material including a conductive metal solution. In embodiments "printing" or "painted" can comprise any method of applying a solution to a material upon which a matrix is desired.

Turning to the figures, in FIG. 1, the dissimilar first electrode 6 and second electrode 10 are applied onto a desired primary surface 2 of an article 4, for example a fabric. In one embodiment a primary surface is a surface of a LLEC or LLEF system that comes into direct contact with an area to be treated such as a skin surface.

In various embodiments the difference of the standard potentials of the electrodes or dots or reservoirs can be in a range from about 0.05 V to approximately about 5.0 V. For example, the standard potential can be about 0.05 V, about 0.06 V, about 0.07 V, about 0.08 V, about 0.09 V, about 0.1 V, about 0.2 V, about 0.3 V, about 0.4 V, about 0.5 V, about 0.6 V, about 0.7 V, about 0.8 V, about 0.9 V, about 1.0 V, about 1.1 V, about 1.2 V, about 1.3 V, about 1.4 V, about 1.5 V, about 1.6 V, about 1.7 V, about 1.8 V, about 1.9 V, about 2.0 V, about 2.1 V, about 2.2 V, about 2.3 V, about 2.4 V, about 2.5 V, about 2.6 V, about 2.7 V, about 2.8 V, about 2.9 V, about 3.0 V, about 3.1 V, about 3.2 V, about 3.3 V, about 3.4 V, about 3.5 V, about 3.6 V, about 3.7 V, about 3.8 V, about 3.9 V, about 4.0 V, about 4.1 V, about 4.2 V, about 4.3 V, about 4.4 V, 4.5 V, about 4.6 V, about 4.7 V, 4.8 V, about 4.9 V, about 5.0 V, about 5.1 V, about 5.2 V, about 5.3 V, about 5.4 V, about 5.5 V, about 5.6 V, about 5.7 V, about 5.8 V, about 5.9 V, about 6.0 V, about 6.1 V, about 6.2 V, about 6.3 V, about 6.4 V, about 6.5 V, about 6.6 V, about 6.7 V, about 6.8 V, about 6.9 V, about 7.0 V, about 7.1 V, about 7.2 V, about 7.3 V, about 7.4 V, 7.5 V, about 7.6 V, about 7.7 V, 7.8 V, about 7.9 V, about 8.0 V, about 8.1 V, about 8.2 V, about 8.3 V, about 8.4 V, about 8.5 V, about 8.6 V, about 8.7 V, about 8.8 V, about 8.9 V, about 9.0 V, or the like.

In embodiments, systems and devices disclosed herein can produce a low level electric current of between for example about 1 and about 200 micro-amperes, between about 10 and about 190 micro-amperes, between about 20 and about 180 micro-amperes, between about 30 and about 170 micro-amperes, between about 40 and about 160 micro-amperes, between about 50 and about 150 micro-amperes, between about 60 and about 140 micro-amperes, between about 70 and about 130 micro-amperes, between about 80 and about 120 micro-amperes, between about 90 and about 100 micro-amperes, between about 100 and about 150 micro-amperes, between about 150 and about 200 micro-amperes, between about 200 and about 250 micro-amperes, between about 250 and about 300 micro-amperes, between about 300 and about 350 micro-amperes, between about 350 and about 400 micro-amperes, between about 400 and about 450 micro-amperes, between about 450 and about 500 micro-amperes, between about 500 and about 550 micro-amperes, between about 550 and about 600 micro-amperes, between about 600 and about 650 micro-amperes, between about 650 and about 700 micro-amperes, between about 700 and about 750 micro-amperes, between about 750 and about 800 micro-amperes, between about 800 and about 850 micro-amperes, between about 850 and about 900 micro-amperes, between about 900 and about 950 micro-amperes, between about 950 and about 1000 micro-amperes (1 milliamp [mA]), between about 1.0 and about 1.1 mA, between about 1.1 and about 1.2 mA, between about 1.2 and about 1.3 mA, between about 1.3 and about 1.4 mA, between about 1.4 and about 1.5 mA, between about 1.5 and about 1.6 mA, between about 1.6 and about 1.7 mA, between about 1.7 and about 1.8 mA, between about 1.8 and about 1.9 mA, between about 1.9 and about 2.0 mA, between about 2.0 and about 2.1 mA, between about 2.1 and about 2.2 mA, between about 2.2 and about 2.3 mA, between about 2.3 and about 2.4 mA, between about 2.4 and about 2.5 mA, between about 2.5 and about 2.6 mA, between about 2.6 and about 2.7 mA, between about 2.7 and about 2.8 mA, between about 2.8 and about 2.9 mA, between about 2.9 and about 3.0 mA, between about 3.0 and about 3.1 mA, between about 3.1 and about 3.2 mA, between about 3.2 and about 3.3 mA, between about 3.3 and about 3.4 mA, between about 3.4 and about 3.5 mA, between about 3.5 and about 3.6 mA, between about 3.6 and about 3.7 mA, between about 3.7 and about 3.8 mA, between about 3.8 and about 3.9 mA, between about 3.9 and about 4.0 mA, between about 4.0 and about 4.1 mA, between about 4.1 and about 4.2 mA, between about 4.2 and about 4.3 mA, between about 4.3 and about 4.4 mA, between about 4.4 and about 4.5 mA, between about 4.5 and about 5.0 mA, between about 5.0 and about 5.5 mA, between about 5.5 and about 6.0 mA, between about 6.0 and about 6.5 mA, between about 6.5 and about 7.0 mA, between about 7.5 and about 8.0 mA, between about 8.0 and about 8.5 mA, between about 8.5 and about 9.0 mA, between about 9.0 and about 9.5 mA, between about 9.5 and about 10.0 mA, between about 10.0 and about 10.5 mA, between about 10.5 and about 11.0 mA, between about 11.0 and about 11.5 mA, between about 11.5 and about 12.0 mA, between about 12.0 and about 12.5 mA, between about 12.5 and about 13.0 mA, between about 13.0 and about 13.5 mA, between about 13.5 and about 14.0 mA, between about 14.0 and about 14.5 mA, between about 14.5 and about 15.0 mA, or the like.

In embodiments, systems and devices disclosed herein can produce a low level electric current of between for example about 1 and about 400 micro-amperes, between about 20 and about 380 micro-amperes, between about 40 and about 360 micro-amperes, between about 60 and about 340 micro-amperes, between about 80 and about 320 micro-amperes, between about 100 and about 300 micro-amperes, between about 120 and about 280 micro-amperes, between about 140 and about 260 micro-amperes, between about 160 and about 240 micro-amperes, between about 180 and about 220 micro-amperes, or the like.

In embodiments, systems and devices disclosed herein can produce a low level electric current of between for example about 1 micro-ampere and about 1 milli-ampere, between about 50 and about 800 micro-amperes, between about 200 and about 600 micro-amperes, between about 400 and about 500 micro-amperes, or the like.

In embodiments, systems and devices disclosed herein can produce a low level electric current of about 10 micro-amperes, about 20 micro-amperes, about 30 micro-amperes, about 40 micro-amperes, about 50 micro-amperes, about 60 micro-amperes, about 70 micro-amperes, about 80 micro-amperes, about 90 micro-amperes, about 100 micro-amperes, about 110 micro-amperes, about 120 micro-amperes, about 130 micro-amperes, about 140 micro-amperes, about 150 micro-amperes, about 160 micro-amperes, about 170 micro-amperes, about 180 micro-amperes, about 190 micro-amperes, about 200 micro-amperes, about 210 micro-amperes, about 220 micro-amperes, about 240 micro-amperes, about 260 micro-amperes, about 280 micro-amperes, about 300 micro-amperes, about 320 micro-amperes, about 340 micro-amperes, about 360 micro-amperes, about 380 micro-amperes, about 400 micro-amperes, about 450 micro-amperes, about 500 micro-amperes, about 550 micro-amperes, about 600 micro-amperes, about 650 micro-amperes, about 700 micro-amperes, about 750 micro-amperes, about 800 micro-amperes, about 850 micro-amperes, about 900 micro-amperes, about 950 micro-amperes, about 1 milli-ampere (mA), about 1.1 mA, about 1.2 mA, about 1.3 mA, about 1.4 mA, about 1.5 mA, about 1.6 mA, about 1.7 mA, about 1.8 mA, about 1.9 mA, about 2.0 mA, about 2.1 mA, about 2.2 mA, about 2.3 mA, about 2.4 mA, about 2.5 mA, about 2.6 mA, about 2.7 mA, about 2.8 mA, about 2.9 mA, about 3.0 mA, about 3.1 mA, about 3.2 mA, about 3.3 mA, about 3.4 mA, about 3.5 mA, about 3.6 mA, about 3.7 mA, about 3.8 mA, about 3.9 mA, about 4.0 mA, about 4.1 mA, about 4.2 mA, about 4.3 mA, about 4.4 mA, about 4.5 mA, about 4.6 mA, about 4.7 mA, about 4.8 mA, about 4.9 mA, about 5.0 mA, about 5.1 mA, about 5.2 mA, about 5.3 mA, about 5.4 mA, about 5.5 mA, about 5.6 mA, about 5.7 mA, about 5.8 mA, about 5.9 mA, about 6.0 mA, about 6.1 mA, about 4.2 mA, about 6.3 mA, about 6.4 mA, about 6.5 mA, about 6.6 mA, about 6.7 mA, about 6.8 mA, about 6.9 mA, about 7.0 mA, about 7.1 mA, about 7.2 mA, about 7.3 mA, about 7.4 mA, about 7.5 mA, about 7.6 mA, about 7.7 mA, about 7.8 mA, about 7.9 mA, about 8.0 mA, about 8.1 mA, about 8.2 mA, about 8.3 mA, about 8.4 mA, about 8.5 mA, about 8.6 mA, about 8.7 mA, about 8.8 mA, about 8.9 mA, about 9.0 mA, about 9.1 mA, about 9.2 mA, about 9.3 mA, about 9.4 mA, about 9.5 mA, about 9.6 mA, about 9.7 mA, about 9.8 mA, about 9.9 mA, about 10.0 mA, about 10.1 mA, about 10.2 mA, about 10.3 mA, about 10.4 mA, about 10.5 mA, about 10.6 mA, about 10.7 mA, about 10.8 mA, about 10.9 mA, about 11.0 mA, about 11.1 mA, about 11.2 mA, about 11.3 mA, about 11.4 mA, about 11.5 mA, about 11.6 mA, about 11.7 mA, about 11.8 mA, about 11.9 mA, about 12.0 mA, about 12.1 mA, about 12.2 mA, about 12.3 mA, about 12.4 mA, about 12.5 mA, about 12.6 mA, about 12.7 mA, about 12.8 mA, about 12.9 mA, about 13.0 mA, about 13.1 mA, about 13.2 mA, about 13.3 mA, about 13.4 mA, about 13.5 mA, about 13.6 mA, about 13.7 mA, about 13.8 mA, about 13.9 mA, about 14.0 mA, about 14.1 mA, about 14.2 mA, about 14.3 mA, about 14.4 mA, about 14.5 mA, about 14.6 mA, about 14.7 mA, about 14.8 mA, about 14.9 mA, about 15.0 mA, about 15.1 mA, about 15.2 mA, about 15.3 mA, about 15.4 mA, about 15.5 mA, about 15.6 mA, about 15.7 mA, about 15.8 mA, or the like.

In embodiments, the disclosed systems and devices can produce a low level electric current of not more than 10 micro-amperes, or not more than about 20 micro-amperes, not more than about 30 micro-amperes, not more than about 40 micro-amperes, not more than about 50 micro-amperes, not more than about 60 micro-amperes, not more than about 70 micro-amperes, not more than about 80 micro-amperes, not more than about 90 micro-amperes, not more than about 100 micro-amperes, not more than about 110 micro-amperes, not more than about 120 micro-amperes, not more than about 130 micro-amperes, not more than about 140 micro-amperes, not more than about 150 micro-amperes, not more than about 160 micro-amperes, not more than about 170 micro-amperes, not more than about 180 micro-amperes, not more than about 190 micro-amperes, not more than about 200 micro-amperes, not more than about 210 micro-amperes, not more than about 220 micro-amperes, not more than about 230 micro-amperes, not more than about 240 micro-amperes, not more than about 250 micro-amperes, not more than about 260 micro-amperes, not more than about 270 micro-amperes, not more than about 280 micro-amperes, not more than about 290 micro-amperes, not more than about 300 micro-amperes, not more than about 310 micro-amperes, not more than about 320 micro-amperes, not more than about 340 micro-amperes, not more than about 360 micro-amperes, not more than about 380 micro-amperes, not more than about 400 micro-amperes, not more than about 420 micro-amperes, not more than about 440 micro-amperes, not more than about 460 micro-amperes, not more than about 480 micro-amperes, not more than about 500 micro-amperes, not more than about 520 micro-amperes, not more than about 540 micro-amperes, not more than about 560 micro-amperes, not more than about 580 micro-amperes, not more than about 600 micro-amperes, not more than about 620 micro-amperes, not more than about 640 micro-amperes, not more than about 660 micro-amperes, not more than about 680 micro-amperes, not more than about 700 micro-amperes, not more than about 720 micro-amperes, not more than about 740 micro-amperes, not more than about 760 micro-amperes, not more than about 780 micro-amperes, not more than about 800 micro-amperes, not more than about 820 micro-amperes, not more than about 840 micro-amperes, not more than about 860 micro-amperes, not more than about 880 micro-amperes, not more than about 900 micro-amperes, not more than about 920 micro-amperes, not more than about 940 micro-amperes, not more than about 960 micro-amperes, not more than about 980 micro-amperes, not more than about 1 milli-ampere (mA), not more than about 1.1 mA, not more than about 1.2 mA, not more than about 1.3 mA, not more than about 1.4 mA, not more than about 1.5 mA, not more than about 1.6 mA, not more than about 1.7 mA, not more than about 1.8 mA, not more than about 1.9 mA, not more than about 2.0 mA, not more than about 2.1 mA, not more than about 2.2 mA, not more than about 2.3 mA, not more than about 2.4 mA, not more than about 2.5 mA, not more than about 2.6 mA, not more than about 2.7 mA, not more than about 2.8 mA, not more than about 2.9 mA, not more than about 3.0 mA, not more than about 3.1 mA, not more than about 3.2 mA, not more than about 3.3 mA, not more than about 3.4 mA, not more than about 3.5 mA, not more than about 3.6 mA, not more than about 3.7 mA, not more than about 3.8 mA, not more than about 3.9 mA, not more than about 4.0 mA, not more than about 4.1 mA, not more than about 4.2 mA, not more than about 4.3 mA, not more than about 4.4 mA, not more than about 4.5 mA, not more than about 4.6 mA, not more than about 4.7 mA, not more than about 4.8 mA, not more than about 4.9 mA, not more than about 5.0 mA, not more than about 5.1 mA, not more than about 5.2 mA, not more than about 5.3 mA, not more than about 5.4 mA, not more than about 5.5 mA, not more than about 5.6 mA, not more than about 5.7 mA, not more than about 5.8 mA, not more than about 5.9 mA, not more than about 6.0 mA, not more than about 6.1 mA, not more than about 4.2 mA, not more than about 6.3 mA, not more than about 6.4 mA, not more than about 6.5 mA, not more than about 6.6 mA, not more than about 6.7 mA, not more than about 6.8 mA, not more than about 6.9 mA, not more than about 7.0 mA, not more than about 7.1 mA, not more than about 7.2 mA, not more than about 7.3 mA, not more than about 7.4 mA, not more than about 7.5 mA, not more than about 7.6 mA, not more than about 7.7 mA, not more than about 7.8 mA, not more than about 7.9 mA, not more than about 8.0 mA, not more than about 8.1 mA, not more than about 8.2 mA, not more than about 8.3 mA, not more than about 8.4 mA, not more than about 8.5 mA, not more than about 8.6 mA, not more than about 8.7 mA, not more than about 8.8 mA, not more than about 8.9 mA, not more than about 9.0 mA, not more than about 9.1 mA, not more than about 9.2 mA, not more than about 9.3 mA, not more than about 9.4 mA, not more than about 9.5 mA, not more than about 9.6 mA, not more than about 9.7 mA, not more than about 9.8 mA, not more than about 9.9 mA, not more than about 10.0 mA, not more than about 10.1 mA, not more than about 10.2 mA, not more than about 10.3 mA, not more than about 10.4 mA, not more than about 10.5 mA, not more than about 10.6 mA, not more than about 10.7 mA, not more than about 10.8 mA, not more than about 10.9 mA, not more than about 11.0 mA, not more than about 11.1 mA, not more than about 11.2 mA, not more than about 11.3 mA, not more than about 11.4 mA, not more than about 11.5 mA, not more than about 11.6 mA, not more than about 11.7 mA, not more than about 11.8 mA, not more than about 11.9 mA, not more than about 12.0 mA, not more than about 12.1 mA, not more than about 12.2 mA, not more than about 12.3 mA, not more than about 12.4 mA, not more than about 12.5 mA, not more than about 12.6 mA, not more than about 12.7 mA, not more than about 12.8 mA, not more than about 12.9 mA, not more than about 13.0 mA, not more than about 13.1 mA, not more than about 13.2 mA, not more than about 13.3 mA, not more than about 13.4 mA, not more than about 13.5 mA, not more than about 13.6 mA, not more than about 13.7 mA, not more than about 13.8 mA, not more than about 13.9 mA, not more than about 14.0 mA, not more than about 14.1 mA, not more than about 14.2 mA, not more than about 14.3 mA, not more than about 14.4 mA, not more than about 14.5 mA, not more than about 14.6 mA, not more than about 14.7 mA, not more than about 14.8 mA, not more than about 14.9 mA, not more than about 15.0 mA, not more than about 15.1 mA, not more than about 15.2 mA, not more than about 15.3 mA, not more than about 15.4 mA, not more than about 15.5 mA, not more than about 15.6 mA, not more than about 15.7 mA, not more than about 15.8 mA, and the like.

In embodiments, systems and devices disclosed herein can produce a low level electric current of not less than 10 micro-amperes, not less than 20 micro-amperes, not less than 30 micro-amperes, not less than 40 micro-amperes, not less than 50 micro-amperes, not less than 60 micro-amperes, not less than 70 micro-amperes, not less than 80 micro-amperes, not less than 90 micro-amperes, not less than 100 micro-amperes, not less than 110 micro-amperes, not less than 120 micro-amperes, not less than 130 micro-amperes, not less than 140 micro-amperes, not less than 150 micro-amperes, not less than 160 micro-amperes, not less than 170 micro-amperes, not less than 180 micro-amperes, not less than 190 micro-amperes, not less than 200 micro-amperes, not less than 210 micro-amperes, not less than 220 micro-amperes, not less than 230 micro-amperes, not less than 240 micro-amperes, not less than 250 micro-amperes, not less than 260 micro-amperes, not less than 270 micro-amperes, not less than 280 micro-amperes, not less than 290 micro-amperes, not less than 300 micro-amperes, not less than 310 micro-amperes, not less than 320 micro-amperes, not less than 330 micro-amperes, not less than 340 micro-amperes, not less than 350 micro-amperes, not less than 360 micro-amperes, not less than 370 micro-amperes, not less than 380 micro-amperes, not less than 390 micro-amperes, not less than 400 micro-amperes, not less than about 420 micro-amperes, not less than about 440 micro-amperes, not less than about 460 micro-amperes, not less than about 480 micro-amperes, not less than about 500 micro-amperes, not less than about 520 micro-amperes, not less than about 540 micro-amperes, not less than about 560 micro-amperes, not less than about 580 micro-amperes, not less than about 600 micro-amperes, not less than about 620 micro-amperes, not less than about 640 micro-amperes, not less than about 660 micro-amperes, not less than about 680 micro-amperes, not less than about 700 micro-amperes, not less than about 720 micro-amperes, not less than about 740 micro-amperes, not less than about 760 micro-amperes, not less than about 780 micro-amperes, not less than about 800 micro-amperes, not less than about 820 micro-amperes, not less than about 840 micro-amperes, not less than about 860 micro-amperes, not less than about 880 micro-amperes, not less than about 900 micro-amperes, not less than about 920 micro-amperes, not less than about 940 micro-amperes, not less than about 960 micro-amperes, not less than about 980 micro-amperes, not less than about 1 milli-ampere (mA), not less than about 1.1 mA, not less than about 1.2 mA, not less than about 1.3 mA, not less than about 1.4 mA, not less than about 1.5 mA, not less than about 1.6 mA, not less than about 1.7 mA, not less than about 1.8 mA, not less than about 1.9 mA, not less than about 2.0 mA, not less than about 2.1 mA, not less than about 2.2 mA, not less than about 2.3 mA, not less than about 2.4 mA, not less than about 2.5 mA, not less than about 2.6 mA, not less than about 2.7 mA, not less than about 2.8 mA, not less than about 2.9 mA, not less than about 3.0 mA, not less than about 3.1 mA, not less than about 3.2 mA, not less than about 3.3 mA, not less than about 3.4 mA, not less than about 3.5 mA, not less than about 3.6 mA, not less than about 3.7 mA, not less than about 3.8 mA, not less than about 3.9 mA, not less than about 4.0 mA, not less than about 4.1 mA, not less than about 4.2 mA, not less than about 4.3 mA, not less than about 4.4 mA, not less than about 4.5 mA, not less than about 4.6 mA, not less than about 4.7 mA, not less than about 4.8 mA, not less than about 4.9 mA, not less than about 5.0 mA, not less than about 5.1 mA, not less than about 5.2 mA, not less than about 5.3 mA, not less than about 5.4 mA, not less than about 5.5 mA, not less than about 5.6 mA, not less than about 5.7 mA, not less than about 5.8 mA, not less than about 5.9 mA, not less than about 6.0 mA, not less than about 6.1 mA, not less than about 4.2 mA, not less than about 6.3 mA, not less than about 6.4 mA, not less than about 6.5 mA, not less than about 6.6 mA, not less than about 6.7 mA, not less than about 6.8 mA, not less than about 6.9 mA, not less than about 7.0 mA, not less than about 7.1 mA, not less than about 7.2 mA, not less than about 7.3 mA, not less than about 7.4 mA, not less than about 7.5 mA, not less than about 7.6 mA, not less than about 7.7 mA, not less than about 7.8 mA, not less than about 7.9 mA, not less than about 8.0 mA, not less than about 8.1 mA, not less than about 8.2 mA, not less than about 8.3 mA, not less than about 8.4 mA, not less than about 8.5 mA, not less than about 8.6 mA, not less than about 8.7 mA, not less than about 8.8 mA, not less than about 8.9 mA, not less than about 9.0 mA, not less than about 9.1 mA, not less than about 9.2 mA, not less than about 9.3 mA, not less than about 9.4 mA, not less than about 9.5 mA, not less than about 9.6 mA, not less than about 9.7 mA, not less than about 9.8 mA, not less than about 9.9 mA, not less than about 10.0 mA, not less than about 10.1 mA, not less than about 10.2 mA, not less than about 10.3 mA, not less than about 10.4 mA, not less than about 10.5 mA, not less than about 10.6 mA, not less than about 10.7 mA, not less than about 10.8 mA, not less than about 10.9 mA, not less than about 11.0 mA, not less than about 11.1 mA, not less than about 11.2 mA, not less than about 11.3 mA, not less than about 11.4 mA, not less than about 11.5 mA, not less than about 11.6 mA, not less than about 11.7 mA, not less than about 11.8 mA, not less than about 11.9 mA, not less than about 12.0 mA, not less than about 12.1 mA, not less than about 12.2 mA, not less than about 12.3 mA, not less than about 12.4 mA, not less than about 12.5 mA, not less than about 12.6 mA, not less than about 12.7 mA, not less than about 12.8 mA, not less than about 12.9 mA, not less than about 13.0 mA, not less than about 13.1 mA, not less than about 13.2 mA, not less than about 13.3 mA, not less than about 13.4 mA, not less than about 13.5 mA, not less than about 13.6 mA, not less than about 13.7 mA, not less than about 13.8 mA, not less than about 13.9 mA, not less than about 14.0 mA, not less than about 14.1 mA, not less than about 14.2 mA, not less than about 14.3 mA, not less than about 14.4 mA, not less than about 14.5 mA, not less than about 14.6 mA, not less than about 14.7 mA, not less than about 14.8 mA, not less than about 14.9 mA, not less than about 15.0 mA, not less than about 15.1 mA, not less than about 15.2 mA, not less than about 15.3 mA, not less than about 15.4 mA, not less than about 15.5 mA, not less than about 15.6 mA, not less than about 15.7 mA, not less than about 15.8 mA, and the like.

In certain embodiments, reservoir or electrode geometry can comprise shapes including circles, polygons, lines, zigzags, ovals, stars, or any suitable variety. This provides the ability to design/customize surface electric field shapes as well as depth of penetration. For example, in embodiments it can be desirable to employ an electric field of greater strength or depth to achieve optimal treatment.

In embodiments, disclosed devices can provide an electric field of greater than physiological strength to a depth of, at least 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or more.

Reservoir or electrode or dot sizes and concentrations can vary, as these variations can allow for changes in the properties of the electric field created by embodiments of the invention. Certain embodiments provide an electric field at about 1 Volt and then, under normal tissue loads with resistance of 100 to 300K ohms, produce a current in the range of 10 microamperes.

Embodiments disclosed herein can comprise patterns of microcells. The patterns can be designed to produce an electric field, an electric current, or both, over and through tissue such as human skin or fat or muscle. In embodiments the pattern can be designed to produce a specific size, strength, density, shape, or duration of electric field or electric current. In embodiments reservoir or dot size and separation and configuration can be altered.

In embodiments devices disclosed herein can apply an electric field, an electric current, or both, wherein the field, current, or both can be of varying size, strength, density, shape, or duration, in different areas of the embodiment. In embodiments, by specifically sizing the electrodes or reservoirs, the shape(s) of the electric field(s), electric current, or both can be customized, increasing or decreasing localized watt densities and allowing for the design of patterns of electrodes or reservoirs wherein the amount of electric field over a tissue can be adjusted based upon feedback from the tissue or upon an algorithm within sensors operably connected to the embodiment and a control module. The electric field, electric current, or both can be greater in one zone of the device or system and lesser in another. The electric field, electric current, or both can change with time and be modulated based on treatment goals or feedback from the tissue or patient. The control module can monitor and adjust the size, strength, density, shape, or duration of electric field or electric current based on tissue parameters. For example, embodiments disclosed herein can produce and maintain localized electrical events. For example, embodiments disclosed herein can produce specific values for the electric field duration, electric field size, electric field shape, field depth, current, polarity, and/or voltage of the device or system.

Devices disclosed herein can generate a localized electric field in a pattern determined by the distance and physical orientation of the dots, cells, or electrodes. Effective depth of the electric field can be predetermined by the orientation and distance between the cells or electrodes.

In embodiments the electric field can be extended, for example through the use of a hydrogel.

In certain embodiments, for example treatment methods, it can be preferable to utilize AC or DC current. For example, embodiments disclosed herein can employ phased array, pulsed, square wave, sinusoidal, or other wave forms, combinations, or the like. Certain embodiments utilize a controller to produce and control power production and/or distribution to the device.

A system or device disclosed herein and placed over tissue such as skin can move relative to the tissue. Reducing the amount of motion between tissue and device can be advantageous to treatment. Slotting or placing cuts into the device can result in less friction or tension on the skin. In embodiments, use of an elastic dressing similar to the elasticity of the skin is also disclosed.

Embodiments can include coatings on the surface of the substrate, such as, for example, over or between the dots, electrodes, or cells. Such coatings can include, for example, silicone, an electrolytic mixture, hypoallergenic agents, drugs, biologics, stem cells, skin substitutes, cosmetic products, combinations thereof, or the like. Drugs suitable for use with embodiments of the invention include analgesics, antibiotics, anti-inflammatories, or the like. Embodiments can include multi-phase systems, for example wherein one array is on a substrate, and another array is suspended, for example in a gel, for example a hydrogel.

The applied electrodes or reservoirs or dots can adhere or bond to the primary surface or substrate because a biocompatible binder is mixed, in embodiments into separate mixtures, with each of the dissimilar metals that will create the pattern of voltaic cells, in embodiments. Most inks are simply a carrier, and a binder mixed with pigment. Similarly, conductive metal solutions can be a binder mixed with a conductive element. The resulting conductive metal solutions can be used with an application method such as screen printing to apply the electrodes to the primary surface in predetermined patterns. Once the conductive metal solutions dry and/or cure, the patterns of spaced electrodes can substantially maintain their relative position, even on a flexible material such as that used for a LLEC or LLEF system. The conductive metal solution can be allowed to dry before being applied to a surface so that the conductive materials do not mix, which could interrupt the array and cause direct reactions that will release the elements.

In certain embodiments that utilize a poly-cellulose binder, the binder itself can have a beneficial effect such as reducing the local concentration of matrix metallo-proteases through an iontophoretic process that drives the cellulose into the surrounding tissue. This process can be used to electronically drive other components such as drugs into the surrounding tissue.

The binder can comprise any biocompatible liquid material that can be mixed with a conductive element (preferably metallic crystals of silver or zinc) to create a conductive solution which can be applied as a thin coating to a microsphere. One suitable binder is a solvent reducible polymer, such as the polyacrylic non-toxic silk-screen ink manufactured by COLORCON® Inc., a division of Berwind Pharmaceutical Services, Inc. (see COLORCON® NO-TOX® product line, part number NT28). In an embodiment the binder is mixed with high purity (at least 99.99%, in an embodiment) metallic silver crystals to make the silver conductive solution. The silver crystals, which can be made by grinding silver into a powder, are preferably smaller than 100 microns in size or about as fine as flour. In an embodiment, the size of the crystals is about 325 mesh, which is typically about 40 microns in size or a little smaller. The binder is separately mixed with high purity (at least 99.99%, in an embodiment) metallic zinc powder which has also preferably been sifted through standard 325 mesh screen, to make the zinc conductive solution. In certain embodiments, the dots or electrodes can comprise a metal content of less than 100%.

Other powders of metal can be used to make other conductive metal solutions in the same way as described in other embodiments.

The size of the metal crystals, the availability of the surface to the conductive fluid and the ratio of metal to binder affects the release rate of the metal from the mixture. When COLORCON® polyacrylic ink is used as the binder, about 10 to 40 percent of the mixture should be metal for a long term bandage (for example, one that stays on for about 10 days). For example, for a longer term LLEC or LLEF system the percent of the mixture that should be metal can be 8 percent, or 10 percent, 12 percent, 14 percent, 16 percent, 18 percent, 20 percent, 22 percent, 24 percent, 26 percent, 28 percent, 30 percent, 32 percent, 34 percent, 36 percent, 38 percent, 40 percent, 42 percent, 44 percent, 46 percent, 48 percent, 50 percent, or the like.

If the same binder is used, but the percentage of the mixture that is metal is increased to 60 percent or higher, a typical system will be effective for longer. For example, for a longer term device, the percent of the mixture that should be metal can be 40 percent, or 42 percent, 44 percent, 46 percent, 48 percent, 50 percent, 52 percent, 54 percent, 56 percent, 58 percent, 60 percent, 62 percent, 64 percent, 66 percent, 68 percent, 70 percent, 72 percent, 74 percent, 76 percent, 78 percent, 80 percent, 82 percent, 84 percent, 86 percent, 88 percent, 90 percent, or the like.

For LLEC or LLEF systems comprising a pliable substrate it can be desired to decrease the percentage of metal down to 5 percent or less, or to use a binder that causes the crystals to be more deeply embedded, so that the primary surface will be antimicrobial for a very long period of time and will not wear prematurely. Other binders can dissolve or otherwise break down faster or slower than a polyacrylic ink, so adjustments can be made to achieve the desired rate of spontaneous reactions from the voltaic cells.

To maximize the number of voltaic cells, in various embodiments, a pattern of alternating silver masses or electrodes or reservoirs and zinc masses or electrodes or reservoirs can create an array of electrical currents across the primary surface. A basic pattern, shown in FIG. 1, has each mass of silver equally spaced from four masses of zinc, and has each mass of zinc equally spaced from four masses of silver, according to an embodiment. The first electrode 6 is separated from the second electrode 10 by a spacing 8. The designs of first electrode 6 and second electrode 10 are simply round dots, and in an embodiment, are repeated. Numerous repetitions 12 of the designs result in a pattern. For an exemplary device comprising silver and zinc, each silver design preferably has about twice as much mass as each zinc design, in an embodiment. For the pattern in FIG. 1, the silver designs are most preferably about a millimeter from each of the closest four zinc designs, and vice-versa. The resulting pattern of dissimilar metal masses defines an array of voltaic cells when introduced to an electrolytic solution. Further disclosure relating to methods of producing micro-arrays can be found in U.S. Pat. No. 7,813,806 entitled CURRENT PRODUCING SURFACE FOR TREATING BIOLOGIC TISSUE issued Oct. 12, 2010, which is incorporated by reference in its entirety.

Figure 2:
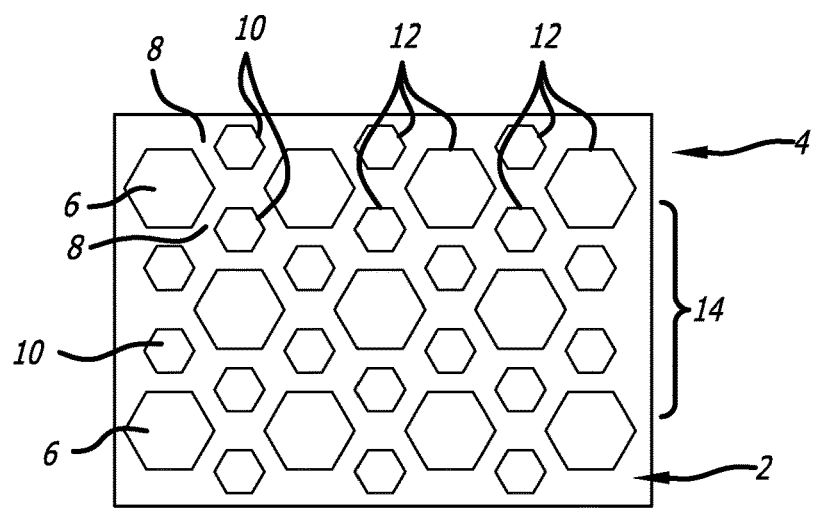
FIG. 2 is a detailed plan view of a pattern of applied electrical conductors in accordance with an embodiment disclosed herein.

A dot pattern of masses like the alternating round dots of FIG. 1 can be preferred when applying conductive material onto a flexible material, such as those used for an article of clothing such as a shirt, shorts, sleeves, or socks, as the dots won't significantly affect the flexibility of the material. To maximize the density of electrical current over a primary surface the pattern of FIG. 2 can be used. The first electrode 6 in FIG. 2 is a large hexagonally shaped dot, and the second electrode 10 is a pair of smaller hexagonally shaped dots that are spaced from each other. The spacing 8 that is between the first electrode 6 and the second electrode 10 maintains a relatively consistent distance between adjacent sides of the designs. Numerous repetitions 12 of the designs result in a pattern 14 that can be described as at least one of the first design being surrounded by six hexagonally shaped dots of the second design.

Figure 3:
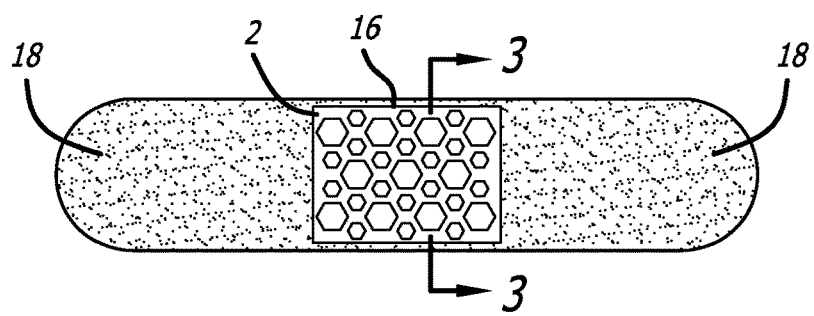
FIG. 3 is an embodiment using the applied pattern of FIG. 2.
Figure 4:
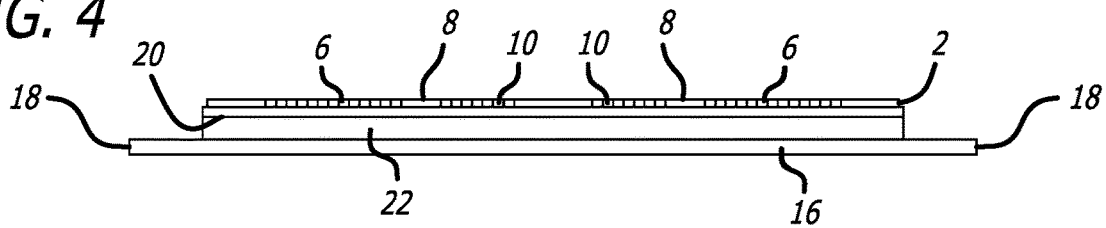
FIG. 4 is a cross-section of FIG. 3 through line 3-3.

FIGS. 3 and 4 show how the pattern of FIG. 2 can be used to make an embodiment disclosed herein. The pattern shown in detail in FIG. 2 is applied to the primary surface 2 of an embodiment. The back 20 of the printed material is fixed to a substrate layer 22. This layer is adhesively fixed to a pliable layer 16.

Figure 5:
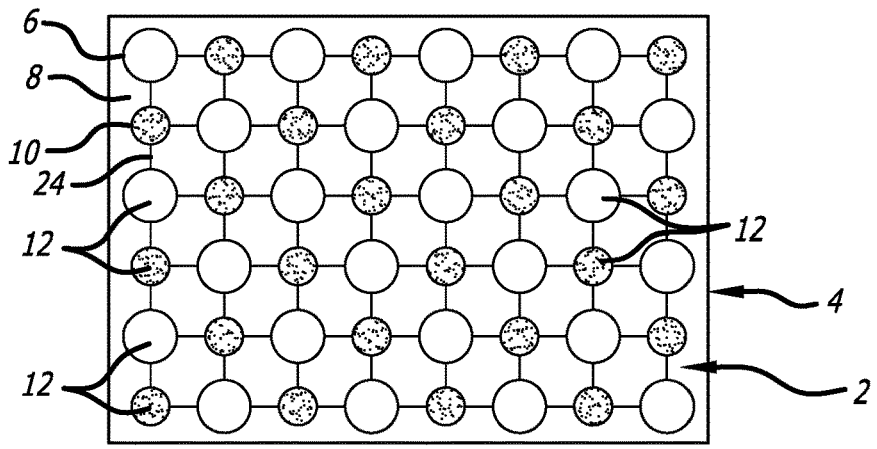
FIG. 5 is a detailed plan view of an alternate embodiment disclosed herein which includes fine lines of conductive metal solution connecting electrodes.

FIG. 5 shows an additional feature, which can be added between designs, that can initiate the flow of current in a poor electrolytic solution. A fine line 24 is printed using one of the conductive metal solutions along a current path of each voltaic cell. The fine line will initially have a direct reaction but will be depleted until the distance between the electrodes increases to where maximum voltage is realized. The initial current produced is intended to help control edema so that the LLEC system will be effective. If the electrolytic solution is highly conductive when the system is initially applied the fine line can be quickly depleted and the device will function as though the fine line had never existed.

Figure 6:
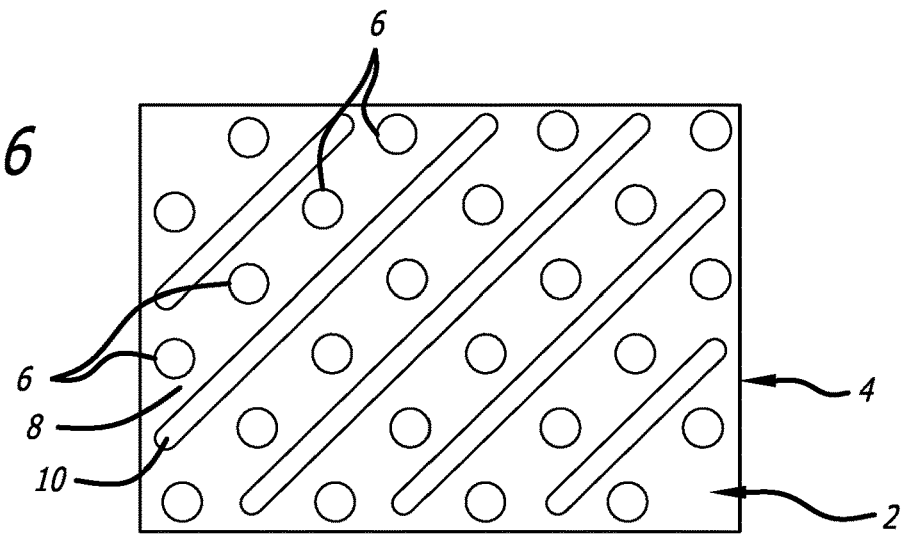
FIG. 6 is a detailed plan view of another alternate embodiment having a line pattern and dot pattern.
Figure 7:
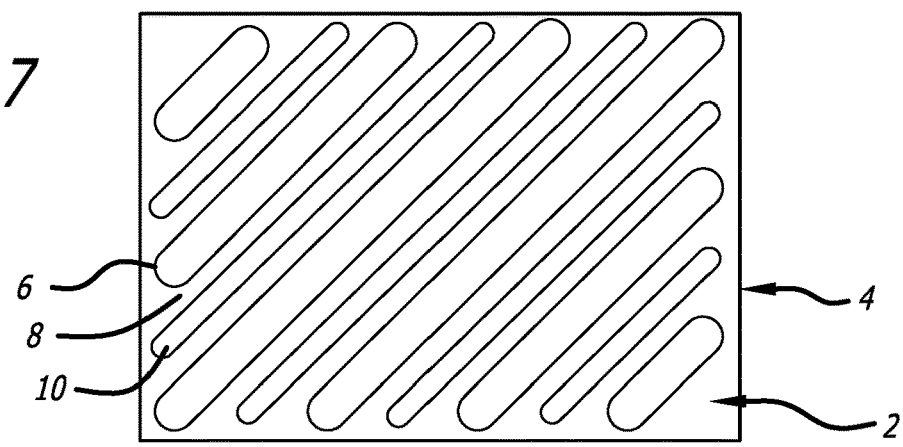
FIG. 7 is a detailed plan view of yet another alternate embodiment having two line patterns.
Figure 8A:
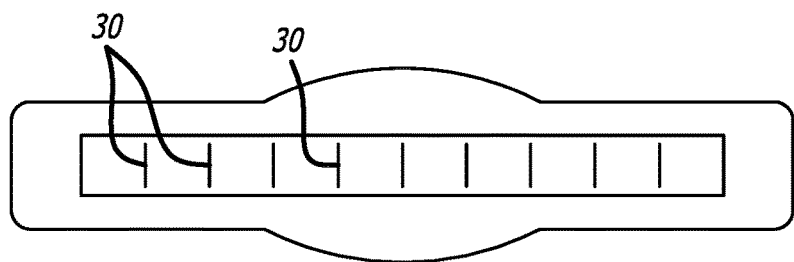
FIGS. 8A-8E depict alternate embodiments showing the location of discontinuous regions as well as anchor regions of the system.
Figure 8B:
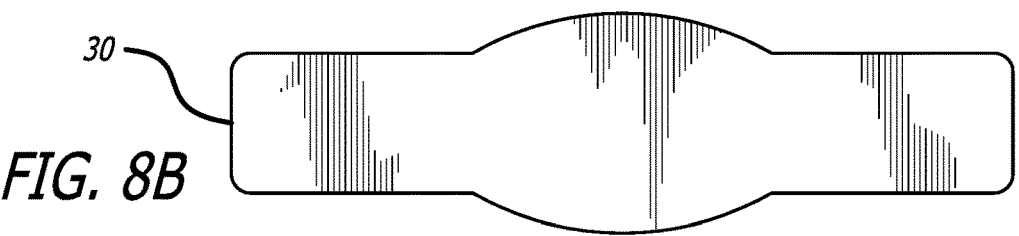
Figure 8C:
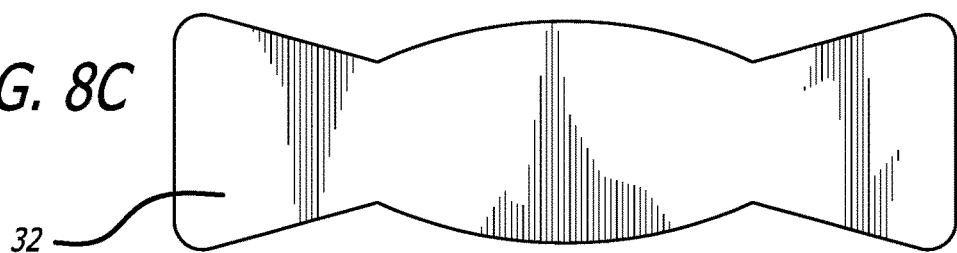
Figure 8D:
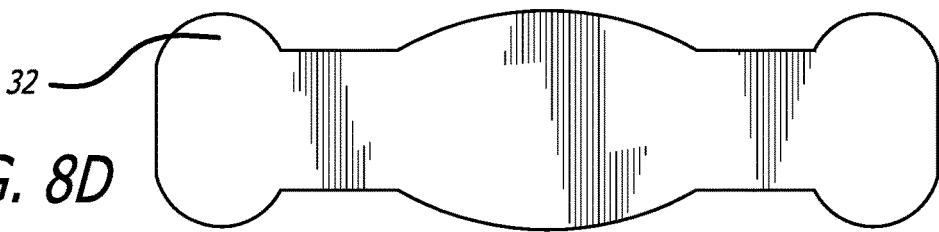
Figure 8E:
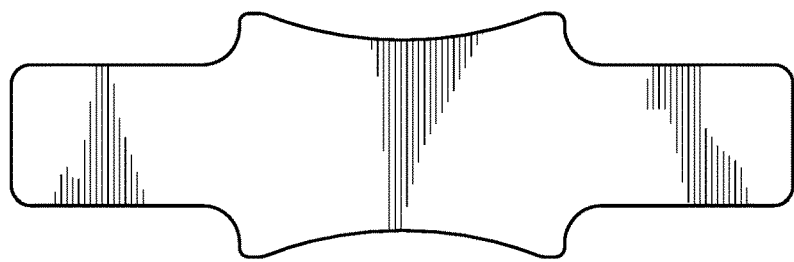

FIGS. 6 and 7 show alternative patterns that use at least one line design. The first electrode 6 of FIG. 6 is a round dot similar to the first design used in FIG. 1. The second electrode 10 of FIG. 6 is a line. When the designs are repeated, they define a pattern of parallel lines that are separated by numerous spaced dots. FIG. 7 uses only line designs. The first electrode 6 can be thicker or wider than the second electrode 10 if the oxidation-reduction reaction requires more metal from the first conductive element (mixed into the first design's conductive metal solution) than the second conductive element (mixed into the second design's conductive metal solution). The lines can be dashed. Another pattern can be silver grid lines that have zinc masses in the center of each of the cells of the grid. The pattern can be letters printed from alternating conductive materials so that a message can be printed onto the primary surface-perhaps a brand name or identifying information such as patient blood type.

Because the spontaneous oxidation-reduction reaction of silver and zinc uses a ratio of approximately two silver to one zinc, the silver design can contain about twice as much mass as the zinc design in an embodiment. At a spacing of about 1 mm between the closest dissimilar metals (closest edge to closest edge) each voltaic cell that contacts a conductive fluid such as a cosmetic cream can create approximately 1 volt of potential that will penetrate substantially through its surrounding surfaces. Closer spacing of the dots can decrease the resistance, providing less potential, and the current will not penetrate as deeply. Therefore, spacing between the closest conductive materials can be, for example, 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, 50 µm, 51 µm, 52 µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm, 70 µm, 71 µm, 72 µm, 73 µm, 74 µm, 75 µm, 76 µm, 77 µm, 78 µm, 79 µm, 80 µm, 81 µm, 82 µm, 83 µm, 84 µm, 85 µm, 86 µm, 87 µm, 88 µm, 89 µm, 90 µm, 91 µm, 92 µm, 93 µm, 94 µm, 95 µm, 96 µm, 97 µm, 98 µm, 99 µm, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

In certain embodiments the spacing between the closest conductive materials can be not more than 0.1 mm, or not more than 0.2 mm, not more than 0.3 mm, not more than 0.4 mm, not more than 0.5 mm, not more than 0.6 mm, not more than 0.7 mm, not more than 0.8 mm, not more than 0.9 mm, not more than 1 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5 mm, not more than 5.1 mm, not more than 5.2 mm, not more than 5.3 mm, not more than 5.4 mm, not more than 5.5 mm, not more than 5.6 mm, not more than 5.7 mm, not more than 5.8 mm, not more than 5.9 mm, not more than 6 mm, or the like.

In certain embodiments spacing between the closest conductive materials can be not less than 0.1 mm, or not less than 0.2 mm, not less than 0.3 mm, not less than 0.4 mm, not less than 0.5 mm, not less than 0.6 mm, not less than 0.7 mm, not less than 0.8 mm, not less than 0.9 mm, not less than 1 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5 mm, not less than 5.1 mm, not less than 5.2 mm, not less than 5.3 mm, not less than 5.4 mm, not less than 5.5 mm, not less than 5.6 mm, not less than 5.7 mm, not less than 5.8 mm, not less than 5.9 mm, not less than 6 mm, or the like.

Disclosures of the present specification include LLEC or LLEF systems comprising a primary surface of a material wherein the material is adapted to be applied to an area of tissue such as a muscle; a first electrode design formed from a first conductive liquid that includes a mixture of a polymer and a first element, the first conductive liquid being applied into a position of contact with the primary surface, the first element including a metal species, and the first electrode design including at least one dot or reservoir, wherein selective ones of the at least one dot or reservoir have approximately a 1.5 mm+/−1 mm mean diameter; a second electrode design formed from a second conductive liquid that includes a mixture of a polymer and a second element, the second element including a different metal species than the first element, the second conductive liquid being printed into a position of contact with the primary surface, and the second electrode design including at least one other dot or reservoir, wherein selective ones of the at least one other dot or reservoir have approximately a 2.5 mm+/−2 mm mean diameter; a spacing on the primary surface that is between the first electrode design and the second electrode design such that the first electrode design does not physically contact the second electrode design, wherein the spacing is approximately 1.5 mm+/−1 mm, and at least one repetition of the first electrode design and the second electrode design, the at least one repetition of the first electrode design being substantially adjacent the second electrode design, wherein the at least one repetition of the first electrode design and the second electrode design, in conjunction with the spacing between the first electrode design and the second electrode design, defines at least one pattern of at least one voltaic cell for spontaneously generating at least one electrical current when introduced to an electrolytic solution. Therefore, electrodes, dots or reservoirs can have a mean diameter of 0.2 mm, or 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, or the like.

In further embodiments, electrodes, dots or reservoirs can have a mean diameter of not less than 0.2 mm, or not less than 0.3 mm, not less than 0.4 mm, not less than 0.5 mm, not less than 0.6 mm, not less than 0.7 mm, not less than 0.8 mm, not less than 0.9 mm, not less than 1.0 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2.0 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3.0 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4.0 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5.0 mm, or the like.

In further embodiments, electrodes, dots or reservoirs can have a mean diameter of not more than 0.2 mm, or not more than 0.3 mm, not more than 0.4 mm, not more than 0.5 mm, not more than 0.6 mm, not more than 0.7 mm, not more than 0.8 mm, not more than 0.9 mm, not more than 1.0 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2.0 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3.0 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4.0 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5.0 mm, or the like.

The material concentrations or quantities within and/or the relative sizes (e.g., dimensions or surface area) of the first and second reservoirs can be selected deliberately to achieve various characteristics of the systems' behavior. For example, the quantities of material within a first and second reservoir can be selected to provide an apparatus having an operational behavior that depletes at approximately a desired rate and/or that "dies" after an approximate period of time after activation. In an embodiment the one or more first reservoirs and the one or more second reservoirs are configured to sustain one or more currents for an approximate pre-determined period of time, after activation. It is to be understood that the amount of time that currents are sustained can depend on external conditions and factors (e.g., the quantity and type of activation material), and currents can occur intermittently depending on the presence or absence of activation material. Further disclosure relating to producing reservoirs that are configured to sustain one or more currents for an approximate pre-determined period of time can be found in U.S. Pat. No. 7,904,147 entitled SUBSTANTIALLY PLANAR ARTICLE AND METHODS OF MANUFACTURE issued Mar. 8, 2011, which is incorporated by reference herein in its entirety.

In various embodiments the difference of the standard potentials of the first and second reservoirs can be in a range from about 0.05 V to approximately 5.0 V. For example, the standard potential can be 0.05 V, or 0.06 V, 0.07 V, 0.08 V, 0.09 V, 0.1 V, 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V, 1.6 V, 1.7 V, 1.8 V, 1.9 V, 2.0 V, 2.1 V, 2.2 V, 2.3 V, 2.4 V, 2.5 V, 2.6 V, 2.7 V, 2.8 V, 2.9 V, 3.0 V, 3.1 V, 3.2 V, 3.3 V, 3.4 V, 3.5 V, 3.6 V, 3.7 V, 3.8 V, 3.9 V, 4.0 V, 4.1 V, 4.2 V, 4.3 V, 4.4 V, 4.5 V, 4.6 V, 4.7 V, 4.8 V, 4.9 V, 5.0 V, or the like.

In a particular embodiment, the difference between the standard potentials of the first and second reservoirs can be at least 0.05 V, or at least 0.06 V, at least 0.07 V, at least 0.08 V, at least 0.09 V, at least 0.1 V, at least 0.2 V, at least 0.3 V, at least 0.4 V, at least 0.5 V, at least 0.6 V, at least 0.7 V, at least 0.8 V, at least 0.9 V, at least 1.0 V, at least 1.1 V, at least 1.2 V, at least 1.3 V, at least 1.4 V, at least 1.5 V, at least 1.6 V, at least 1.7 V, at least 1.8 V, at least 1.9 V, at least 2.0 V, at least 2.1 V, at least 2.2 V, at least 2.3 V, at least 2.4 V, at least 2.5 V, at least 2.6 V, at least 2.7 V, at least 2.8 V, at least 2.9 V, at least 3.0 V, at least 3.1 V, at least 3.2 V, at least 3.3 V, at least 3.4 V, at least 3.5 V, at least 3.6 V, at least 3.7 V, at least 3.8 V, at least 3.9 V, at least 4.0 V, at least 4.1 V, at least 4.2 V, at least 4.3 V, at least 4.4 V, at least 4.5 V, at least 4.6 V, at least 4.7 V, at least 4.8 V, at least 4.9 V, at least 5.0 V, or the like.

In a particular embodiment, the difference of the standard potentials of the first and second reservoirs can be not more than 0.05 V, or not more than 0.06 V, not more than 0.07 V, not more than 0.08 V, not more than 0.09 V, not more than 0.1 V, not more than 0.2 V, not more than 0.3 V, not more than 0.4 V, not more than 0.5 V, not more than 0.6 V, not more than 0.7 V, not more than 0.8 V, not more than 0.9 V, not more than 1.0 V, not more than 1.1 V, not more than 1.2 V, not more than 1.3 V, not more than 1.4 V, not more than 1.5 V, not more than 1.6 V, not more than 1.7 V, not more than 1.8 V, not more than 1.9 V, not more than 2.0 V, not more than 2.1 V, not more than 2.2 V, not more than 2.3 V, not more than 2.4 V, not more than 2.5 V, not more than 2.6 V, not more than 2.7 V, not more than 2.8 V, not more than 2.9 V, not more than 3.0 V, not more than 3.1 V, not more than 3.2 V, not more than 3.3 V, not more than 3.4 V, not more than 3.5 V, not more than 3.6 V, not more than 3.7 V, not more than 3.8 V, not more than 3.9 V, not more than 4.0 V, not more than 4.1 V, not more than 4.2 V, not more than 4.3 V, not more than 4.4 V, not more than 4.5 V, not more than 4.6 V, not more than 4.7 V, not more than 4.8 V, not more than 4.9 V, not more than 5.0 V, or the like. In embodiments that include very small reservoirs (e.g., on the nanometer scale), the difference of the standard potentials can be substantially less or more. Further disclosure relating to standard potentials can be found in U.S. Pat. No. 8,224,439 entitled BATTERIES AND METHODS OF MANUFACTURE AND USE issued Jul. 17, 2012, which is incorporated by reference herein in its entirety.

The voltage present at the site of treatment is typically in the range of millivolts, but disclosed embodiments can introduce a much higher voltage, for example near 1 volt when using the 1 mm spacing of dissimilar metals already described. The higher voltage is believed to drive the current deeper into the treatment area. In this way the current not only can drive silver and zinc into the treatment if desired for treatment, but the current can also provide a stimulatory current so that the entire surface area can be treated. The higher voltage may also increase antimicrobial effect bacteria and preventing biofilms. The electric field can also have beneficial effects on cell migration, ATP production, and angiogenesis.

Embodiments disclosed herein relating to tissue treatment can also comprise selecting a patient or tissue in need of, or that could benefit by, the methods described herein.

In embodiments the fabric or dressing can include a port to access the interior, for example to add fluid, gel, cosmetic products, a hydrating material, or some other material to the dressing. Certain embodiments can comprise a "blister" top that can enclose a material such as an antibacterial or a hydrating medium. In embodiments, the blister top can contain a material that is released into or on to the material when the blister is pressed, for example a liquid or cream. For example, embodiments disclosed herein can comprise a blister top containing an antibacterial or the like.

In embodiments the system comprises a component such as lycra or spandex or elastic or other such fabric to maintain or help maintain its position. In certain embodiment the system comprises a compression fabric and exerts a pressure on subject's body. In general, the compression garments described herein may be configured to exert a pressure of between about 2 mm Hg and about 100 mmHg on a surface. In embodiments the pressure applied by the garment can be, for example, between 5 and 90 mmHg, between 10 and 80 mmHg, between 15 and 75 mmHg, between 20 and 70 mmHg, between 25 and 65 mmHg, between 30 and 60 mmHg, between 35 and 55 mmHg, between 40 and 50 mmHg, or the like.

In other embodiments the pressure exerted on subject's body can vary by the type of garment type and the type of tissue injury. For example, a garment shaped to fit a patient's leg can be configured to exert a greater or lesser compression force on the quadriceps than on the lower leg. Additionally, a tissue injury such as a torn rotor cuff or treatment accompanying post tenotomy surgery can require a specific amount of pressure exerted on the tissue injury to keep the tissue or joint immobilized while healing. In this example, a garment or dressing can be shaped to fit the area of the patient's injury and exert a greater or less compression force as prescribed compared to the rest of the garment or dressing.

In embodiments, disclosed systems and/or devices can comprise components such as straps to maintain or help maintain its position. In certain embodiments the system or device comprises a strap on either end of the long axis, or a strap linking on end of the long axis to the other. In embodiments that straps can comprise Velcro or a similar fastening system. In embodiments the straps can comprise elastic materials. In further embodiments the strap can comprise a conductive material, for example a wire or cable to electrically link the device with other components, such as monitoring equipment or a power source.

Aspects disclosed herein include systems, devices, and methods for data collection and/or data transmission, for example using bioelectric devices that comprise a substrate with one or more sensing elements, multi-array matrix of biocompatible microcells which can generate a LLEF or LLEC, and wherein a data element is collected from the sensing element and transmitted by a control module to a external device. Embodiments can include, for example, data collection equipment so as to track and/or quantify a user's movements or performance. Embodiments can include, for example, an accelerometer, so as to measure a user's speed, or impact forces on a user. Embodiments can include optical data collection devices, for example a camera.

In embodiments the device can be mechanically or wirelessly linked to monitoring or data collection equipment, for example linked via Bluetooth to a cell phone or computer that collects data from the device. In certain embodiments, disclosed devices and systems can comprise data collection means, such as location, temperature, pH, pressure, or conductivity data collection means. Embodiments can comprise a display, for example to visually present, for example, the location, temperature, pH, pressure, or conductivity data to a user.

In embodiments, the visual display can indicate when a data reading is outside a desired or approved range. For example, in an embodiment the device can provide a visual or audible warning or alarm when an accelerometer reading indicates an impact greater than the desired range, or a visual or audible warning or alarm when a temperature, pulse, or respiration reading is outside a desired range.

In certain embodiments, a substrate comprising the multi-array matrix can comprise one layer of a composite dressing, for example a composite garment or fabric comprising the substrate, an adhesive layer, an expandable absorbent layer, and a stretchable, expandable film layer. The expandable absorbent layer can absorb excess fluid such as perspiration from the substrate and expand away from the treatment area, thus preventing oversaturation of the treatment area with resultant maceration and increased infection risk.

The stretchable, expandable film layer can stretch to accommodate a larger foam volume as the foam absorbs liquid. This aspect reduces shear forces on the skin. Additionally, the vertically-expanding foam and film allows the dressing to absorb more volume of fluid in a smaller contact area.

In embodiments the system comprises a component such as an adhesive to maintain or help maintain its position. The adhesive component can be covered with a protective layer that can be removed to expose the adhesive at the time of use. In embodiments the adhesive can comprise, for example, sealants, such as hypoallergenic sealants, waterproof sealants such as epoxies, and the like. Straps can include Velcro or similar materials to aid in maintaining the position of the device.

In embodiments the positioning component can comprise an elastic film with an elasticity, for example, similar to that of skin, or greater than that of skin, or less than that of skin. In embodiments, the LLEC or LLEF system can comprise a laminate where layers of the laminate can be of varying elasticities. For example, an outer layer may be highly elastic and an inner layer in-elastic or less elastic. The in-elastic layer can be made to stretch by placing stress relieving discontinuous regions or slits through the thickness of the material so there is a mechanical displacement rather than stress that would break the fabric weave before stretching would occur. In embodiments the slits can extend completely through a layer or the system or can be placed where expansion is required. In embodiments of the system the slits do not extend all the way through the system or a portion of the system such as the substrate. In embodiments the discontinuous regions can pass halfway through the long axis of the substrate.

In embodiments the device can be shaped to fit an area of desired use, for example a muscle, such as cardiac muscle, smooth muscle, or skeletal muscle.

Embodiments disclosed herein comprise biocompatible electrodes or reservoirs or dots on a surface or substrate, for example a fabric, a fiber, or the like. In embodiments the surface or substrate can be pliable, for example to better follow the contours of an area to be treated, such as the face or back. In embodiments the surface or substrate can comprise a gauze or mesh or plastic. Suitable types of pliable surfaces or substrates for use in embodiments disclosed herein can be absorbent or non-absorbent textiles, low-adhesives, vapor permeable films, hydrocolloids, hydrogels, alginates, foams, foam-based materials, cellulose-based materials including Kettenbach fibers, hollow tubes, fibrous materials, such as those impregnated with anhydrous/hygroscopic materials, beads and the like, or any suitable material as known in the art. In embodiments the pliable material can form, for example, a mask, such as that worn on the body, pants, shorts, gloves, socks, shirts or a portion thereof, for example an elastic or compression shirt, or a portion thereof such as a sleeve, wrappings, towels, cloths, fabrics, or the like. Multi layer embodiments can include, for example, a skin-contacting layer, a hydration layer, and a hydration containment layer.

In embodiments the substrate layer can be non-pliable, for example, a plastic such as a pad (for example a shoulder or thigh pad) or a helmet or the like.

A LLEC or LLEF system disclosed herein can comprise "anchor" regions or "arms" or straps to affix the system securely. The anchor regions or arms can anchor the LLEC or LLEF system. For example, a LLEC or LLEF system can be secured to an area proximal to a treatment area, and anchor regions of the system can extend to areas of minimal stress or movement to securely affix the system. Further, the LLEC system can reduce stress on an area, for example by "countering" the physical stress caused by movement.

In embodiments the LLEC or LLEF system can comprise additional materials to aid in treatment, for example a warming gel.

In embodiments, the LLEC or LLEF system can comprise instructions or directions on how to place the system to maximize its performance. Embodiments include a kit comprising an LLEC or LLEF system and directions for its use. Embodiments can include software to integrate the system or device with, for example, a computer, or cellular telephone, or the like.

In certain embodiments dissimilar or similar metals can be used to create an electric field with a desired voltage. In certain embodiments the pattern of reservoirs can control the watt density and shape of the electric field.

Certain embodiments can utilize a power source, for example a battery. The power source can be any energy source capable of generating a current in the LLEC system and can include, for example, AC power, DC power, radio frequencies (RF) such as pulsed RF, induction, ultrasound, and the like. For example, an AC power source can be of any wave form, such as a sine wave, a triangular wave, or a square wave. AC power can also be of any frequency such as for example 50 Hz, or 60 HZ, or the like. AC power can also be of any voltage, such as for example 120 volts, or 220 volts, or the like. In embodiments an AC power source can be electronically modified, such as for example having the voltage reduced, prior to use.

In embodiments the electric field can be extended, for example through the use of a hydrogel. A hydrogel is a network of polymer chains that are hydrophilic. Hydrogels are highly absorbent natural or synthetic polymeric networks. Hydrogels can be configured to contain a high percentage of water (e.g. they can contain over 90% water). Hydrogels can possess a degree of flexibility very similar to natural tissue, due to their significant water content. A hydrogel can be configured in a variety of viscosities. Viscosity is a measurement of a fluid or material's resistance to gradual deformation by shear stress or tensile stress. In embodiments the electrical field can be extended through a semi-liquid hydrogel with a low viscosity such an ointment or a cellular culture medium. In other embodiments the electrical field can be extended through a solid hydrogel with a high viscosity such as a Petri dish, clothing, or material used to manufacture a prosthetic. In general, the hydrogel described herein may be configured to a viscosity of between about 0.5 Pa·s and greater than about $10^{12}$ Pa·s. In embodiments the viscosity of a hydrogel can be, for example, between 0.5 and $10^{12}$ Pa·s, between 1 Pa·s and $10^6$ Pa·s, between 5 and $10^3$ Pa·s, between 10 and 100 Pa·s, between 15 and 90 Pa·s, between 20 and 80 Pa·s, between 25 and 70 Pa·s, between 30 and 60 Pa·s, or the like. In embodiments, the hydrogel can comprise electrolytes to increase their conductivity.

While various embodiments have been shown and described, it will be realized that alterations and modifications can be made thereto without departing from the scope of the following claims. It is expected that other methods of applying the conductive material can be substituted as appropriate. Also, there are numerous shapes, sizes and patterns of voltaic cells that have not been described but it is expected that this disclosure will enable those skilled in the art to incorporate their own designs which will then be applied to a surface to create voltaic cells which will become active when brought into contact with an electrolytic solution.

Certain embodiments include LLEC or LLEF systems comprising embodiments designed to be used on irregular, non-planar, or "stretching" surfaces. Embodiments disclosed herein can be used with numerous irregular surfaces of the body or areas prone to movement, for example the shoulders, the back, the legs, the arms, etc.

In certain embodiments comprising a garment, the garment can be shaped to fit a particular region of the body such as an arm, shoulder, elbow, leg, knee, hip, ankle, or chest. Additionally, a garment can be a compression fabric and can exert a pressure on a subject's body surface to allow stable and continuous positioning of the garment substrate on subject's body.

Figure 9A:
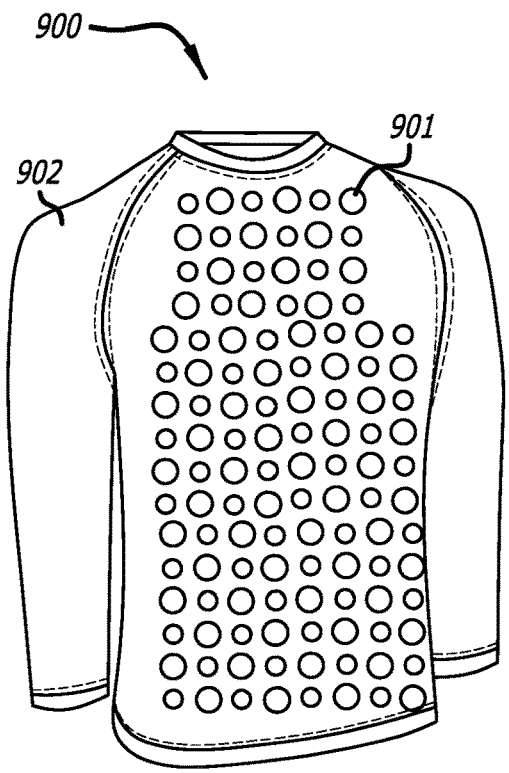
FIGS. 9A-9D depict alternate embodiments showing a garment comprising a multi-array matrix of biocompatible microcells.
Figure 9B:
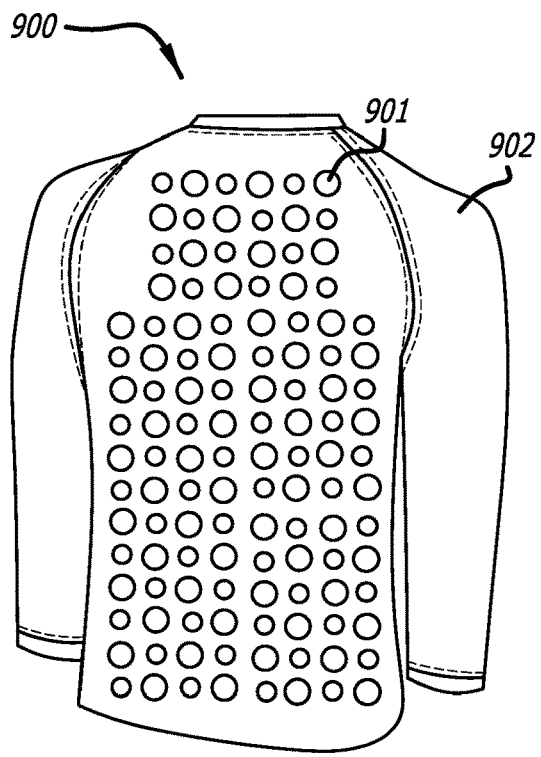
Figure 9C:
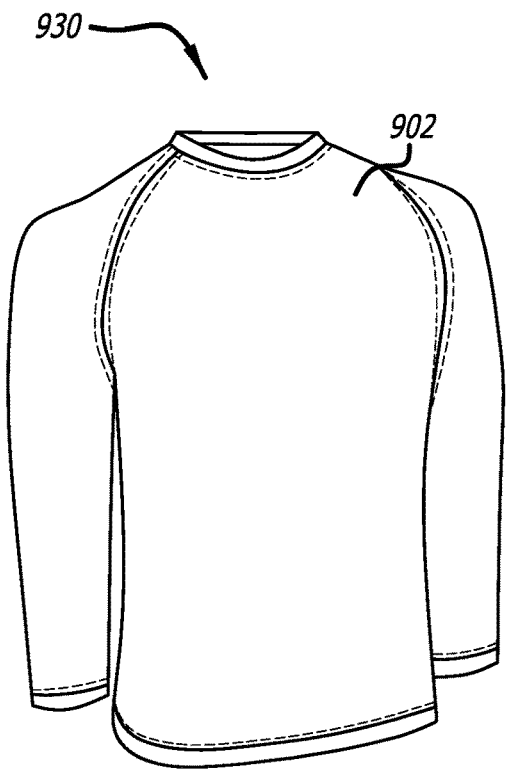
Figure 9D:
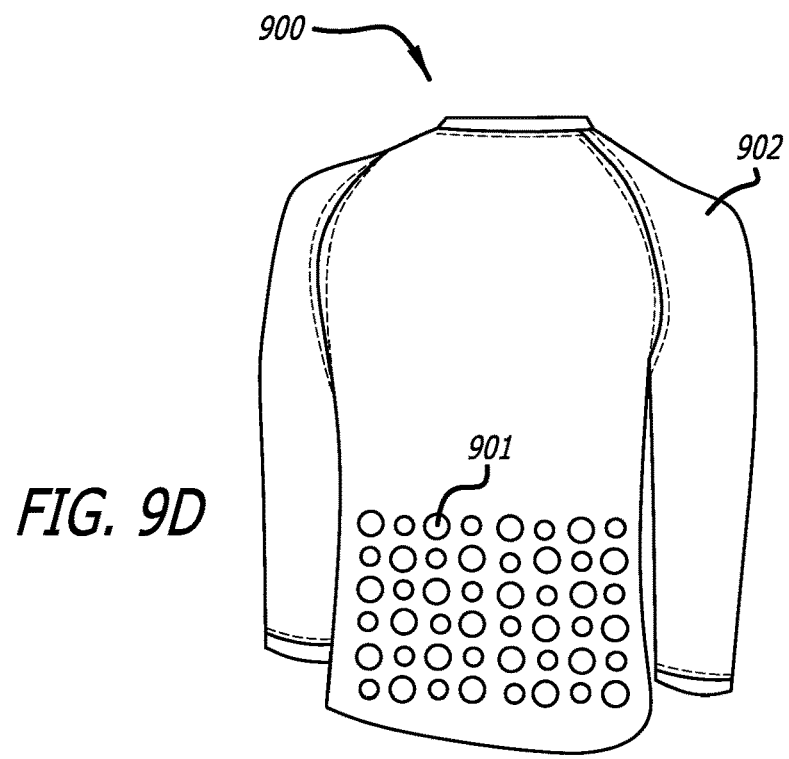

FIG. 9A depicts an example garment 900 comprising a multi-array matrix of biocompatible microcells. Garment 900 comprises electrodes 901 and substrate 902. Electrodes 901 are printed around the entirety of substrate 902 including the back of garment 910. Electrodes 901 can provide a LLEF to tissue, and, when in contact with a conductive material, a LLEC. In another embodiment, electrodes 901 can be printed to a portion of the garment 950, as depicted in FIG. 9B. For example, electrodes 901 can be applied to only the back of garment 960 to provide LLEF to lower back. In certain embodiment, electrodes 901 can also be removed and a new set of dots 901 can be applied to similar or new location on garment (950 & 960). The array can be printed or applied such that it contacts the skin while in use. For example, the array can be printed on or applied to the inside of the garment.

Figure 10:
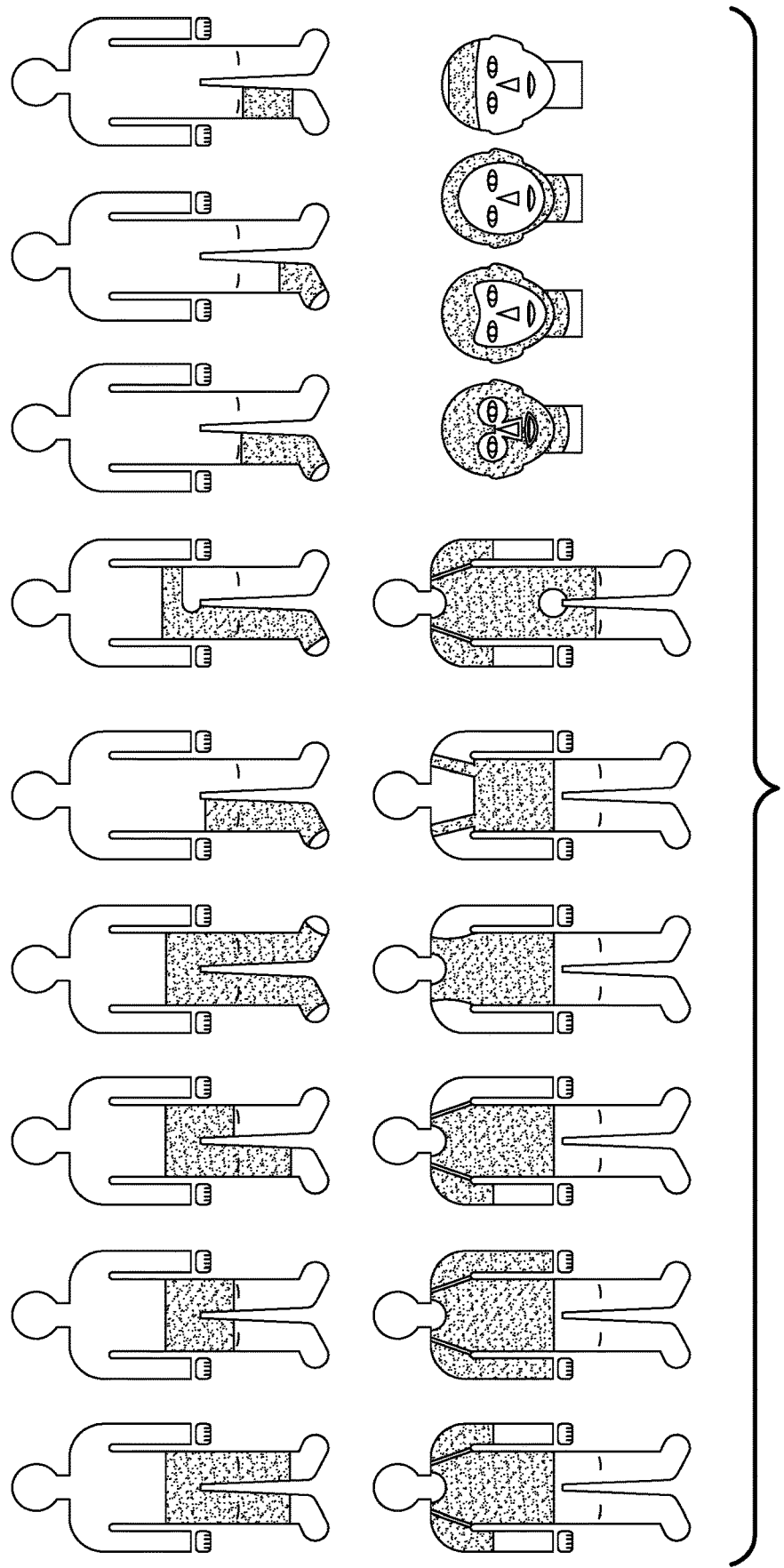
FIG. 10 depicts alternative embodiments showing body placement of garment for treating muscles.

FIG. 10 depicts alternative embodiments showing exemplary garment body placement for treating muscles. In certain embodiments, garments can be configured to be worn over the torso, such as the thoracic, dorsal (back), abdominal, pelvic, pubic, or a combination thereof. In certain embodiments, garment can also be configured to be worn over the extremities, such upper limbs and lower limbs. In certain embodiments, garments can also be configured to be worn over the head, neck, or a combination thereof. Additionally, certain embodiments can be configured to include multiple combinations of the torso, extremities, cephalic, and cervical areas.

Figure 11A:
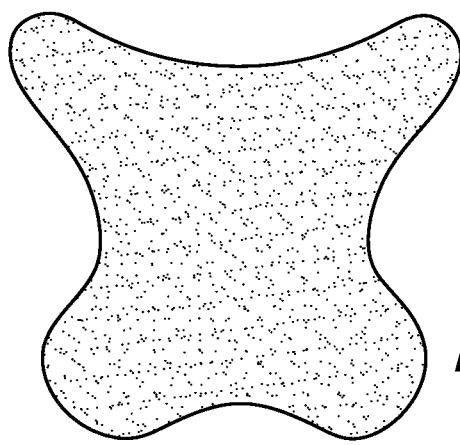
FIGS. 11A-11B depict a "universal" embodiment for use on multiple areas of the body.
Figure 11B:
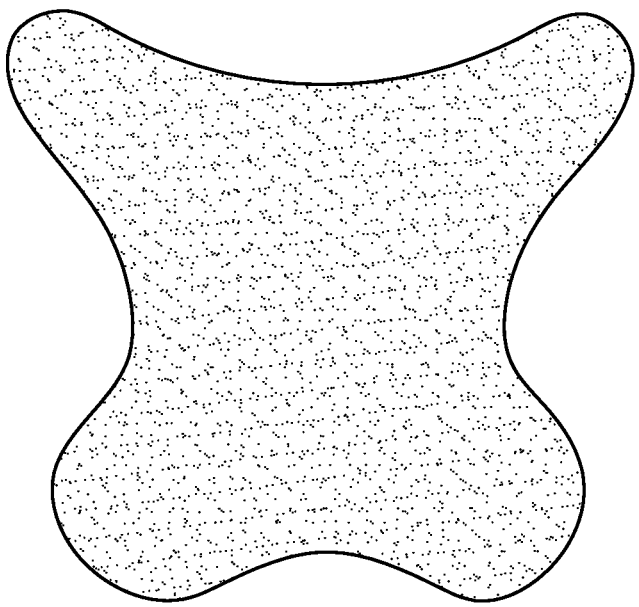
Figure 12D:
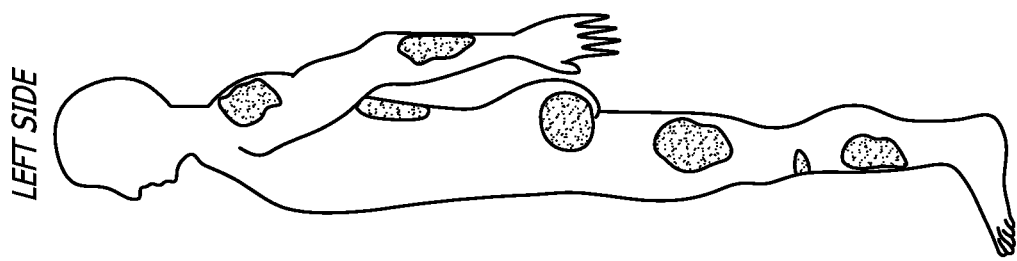
FIGS. 12A-12D depict prospective areas for treatment with the universal embodiment in FIG. 11.
Figure 12C:
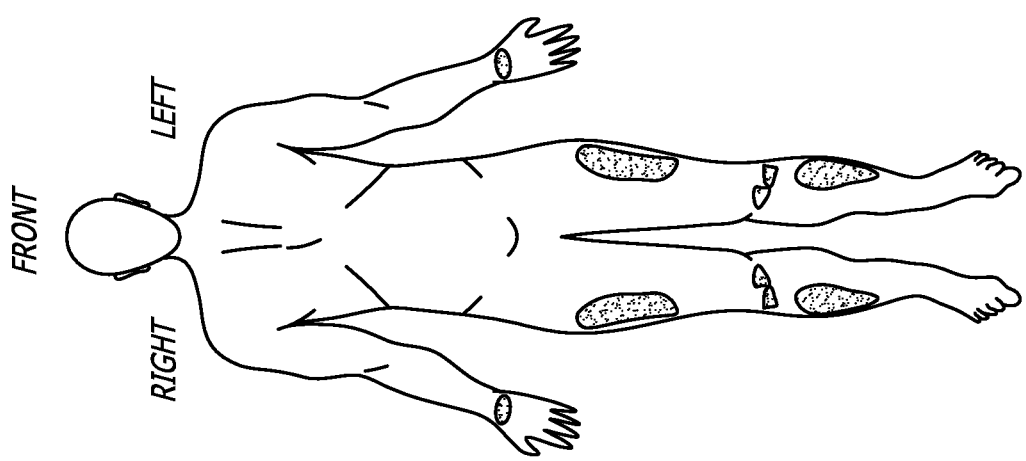
Figure 12B:
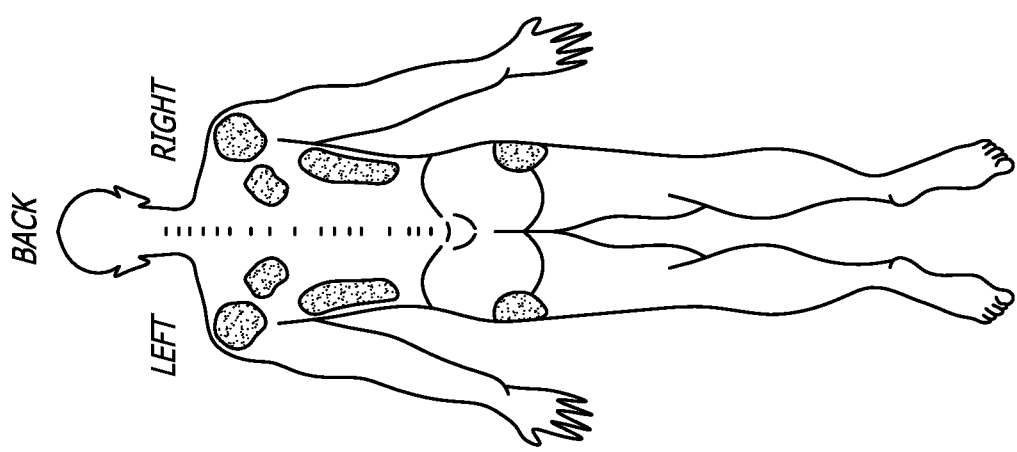
Figure 12A:
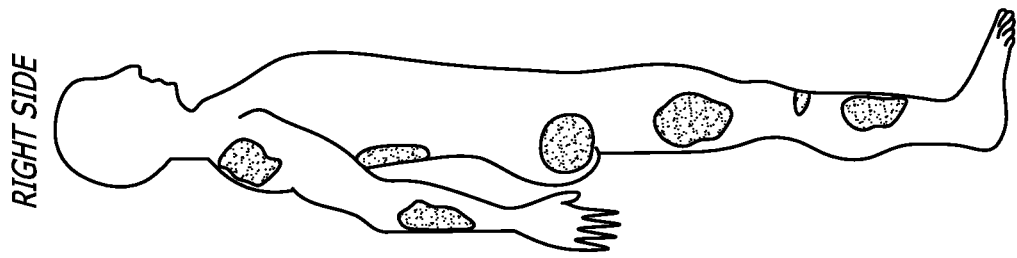

FIG. 11 shows a "universal" embodiment as disclosed herein. The design of the embodiment provides for compatibility with numerous areas of the body. FIG. 12 shows prospective treatment areas using the universal embodiment.

Figure 13:
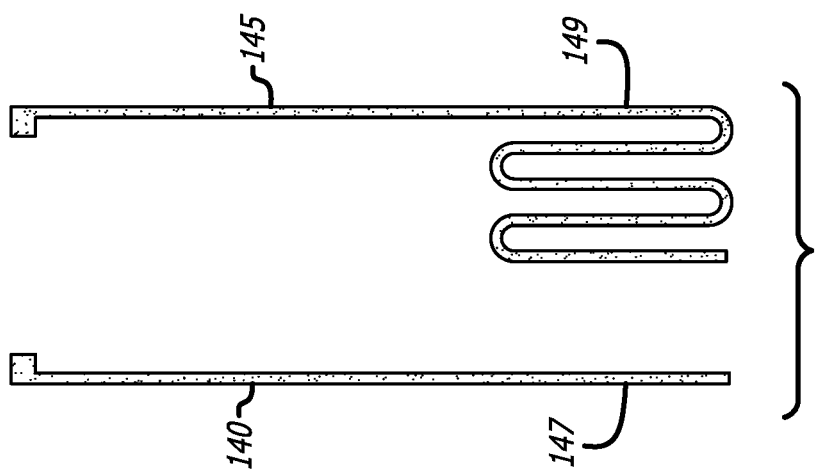
FIG. 13 depicts a detailed plan view of a substrate layer electrode pattern disclosed herein.

FIG. 13 shows an embodiment utilizing two electrodes (one positive and one negative). Upper arms 140 and 145 can be, for example, 1, 2, 3, or 4 mm in width. Lower arm 147 and serpentine 149 can be, for example, 1, 2, 3, or 4 mm in width. The electrodes can be, for example, 1, 2, or 3 mm in depth.

Figure 14:
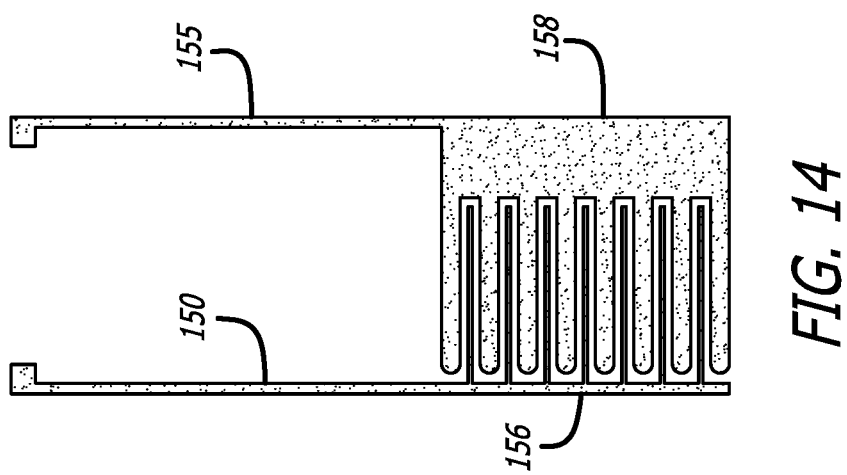
FIG. 14 depicts a detailed plan view of a substrate layer electrode pattern as disclosed herein.

FIG. 14 shows an embodiment utilizing two electrodes (one positive and one negative). Upper arms 150 and 155 can be, for example, 1, 2, 3, or 4 mm in width. The extensions protruding from the lower arm 156 can be, for example, 1, 1.5, 2, 2.5, 3, 3.5, or 4 mm in width. The extensions protruding from the comb 158 can be, for example, 1, 2, 3, 4, 5, 6, or 7 mm in width. The electrodes can be, for example, 1, 2, or 3 mm in depth.

Figure 15:
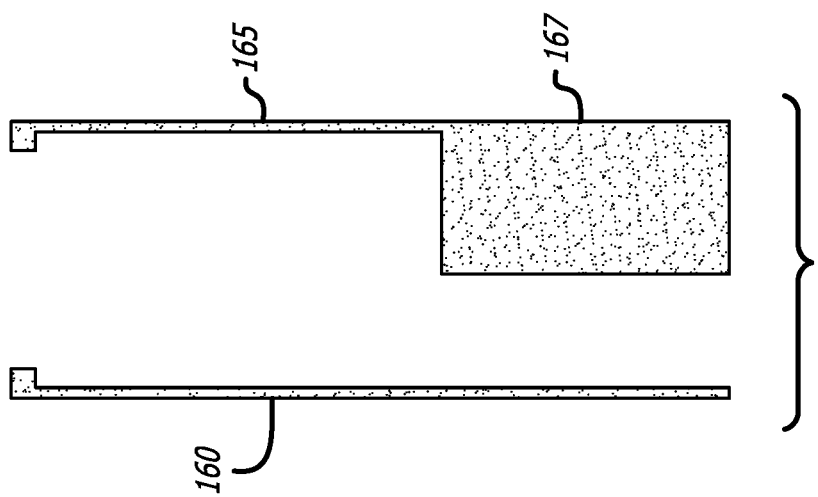
FIG. 15 depicts a detailed plan view of a substrate layer electrode pattern disclosed herein.

FIG. 15 shows an embodiment utilizing two electrodes (one positive and one negative). Upper arms 160 and 165 can be, for example, 1, 2, 3, or 4 mm in width. Lower block 167 can be, for example, 30, 32, 34, 36, 38, 40, 42, 44, 46, 48, 50, 52, or 54 mm along its shorter axis. Lower block 167 can be, for example, 60, 65, 70, 75, 80, 85, 90, 95, or 100 mm along its longer axis. The electrodes can be, for example, 1, 2, or 3 mm in depth.

In embodiments such as those in FIGS. 14-16, the width and depth of the various areas of the electrode can be designed to produce a particular electric field, or, when both electrodes are in contact with a conductive material, a particular electric current. For example, the width of the various areas of the electrode can be, for example, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or 7 mm, or 8 mm, or 9 mm, or 10 mm, or 11 mm, or the like.

In embodiments, the depth or thickness of the various areas of the electrode can be, for example, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

The shortest distance between the two electrodes in an embodiment can be, for example, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, or the like.

In embodiments, the length of the long axis of the device can be, for example, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 75 mm, 100 mm, 150 mm, 200 mm, 250 mm, 300 mm, 350 mm, 400 mm, 450 mm, 500 mm, 600 mm, 700 mm, 800 mm, 900 mm, 1000 mm, or more, or the like.

In embodiments, the length of the short axis of the device can be, for example, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 75 mm, 100 mm, or more, or the like.

Systems and devices disclosed herein can comprise an absorbent foam layer. In embodiments the absorbent foam layer is located on the adhesive layer on the side opposite the substrate layer. In embodiments, the foam comprises water, saline, or an active agent to maintain hydration in the substrate layer.

Certain embodiments disclosed herein include a method of manufacturing a LLEC or LLEF system, the method comprising joining with a substrate multiple first reservoirs wherein selected ones of the multiple first reservoirs include a reducing agent, and wherein first reservoir surfaces of selected ones of the multiple first reservoirs are proximate to a first substrate surface; and joining with the substrate multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises joining using tattooing. In embodiments the substrate can comprise gauzes comprising dots or electrodes.

Further embodiments can include a method of manufacturing a LLEC or LLEF system, the method comprising joining with a substrate multiple first reservoirs wherein selected ones of the multiple first reservoirs include a reducing agent, and wherein first reservoir surfaces of selected ones of the multiple first reservoirs are proximate to a first substrate surface; and joining with the substrate multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises: combining the multiple first reservoirs, the multiple second reservoirs, and multiple parallel insulators to produce a pattern repeat arranged in a first direction across a plane, the pattern repeat including a sequence of a first one of the parallel insulators, one of the multiple first reservoirs, a second one of the parallel insulators, and one of the multiple second reservoirs; and weaving multiple transverse insulators through the first parallel insulator, the one first reservoir, the second parallel insulator, and the one second reservoir in a second direction across the plane to produce a woven apparatus.

In embodiments "ink" or "paint" can comprise any conductive material such as a solution suitable for forming an electrode on a surface, such as a conductive metal solution. In embodiments "printing" or "painted" can comprise any method of applying a conductive material such as a conductive liquid material to a material upon which a matrix is desired, such as a fabric.

In embodiments printing devices can be used to produce LLEC or LLEF systems disclosed herein. For example, inkjet or "3D" printers can be used to produce embodiments.

In certain embodiments the binders or inks used to produce LLEC or LLEF systems disclosed herein can include, for example, poly cellulose inks, poly acrylic inks, poly urethane inks, silicone inks, and the like. In embodiments the type of ink used can determine the release rate of electrons from the reservoirs. In embodiments various materials can be added to the ink or binder such as, for example, conductive or resistive materials can be added to alter the shape or strength of the electric field. Other materials, such as silicone, can be added, for example to enhance scar reduction. Such materials can also be added to the spaces between reservoirs.

In embodiments, fabric embodiments disclosed herein can be woven of at least two types of fibers; fibers comprising sections treated or coated with a substance capable of forming a positive electrode; and fibers comprising sections treated or coated with a substance capable of forming a negative electrode. The fabric can further comprise fibers that do not form an electrode. Long lengths of fibers can be woven together to form fabrics. For example, the fibers can be woven together to form a regular pattern of positive and negative electrodes.

Embodiments disclosed herein include a multilayer fabric, for example a layer that can produce an LLEC/LLEF as described herein, a hydration layer, and a waterproof layer.

In some embodiments, a LLEC or LLEF system can be integrated into a garment or affixed to the garment. For example, the LLEC or LLEF system can be printed directly on a garment while being manufactured or affixed to garment after it has been manufactured. In another embodiment, a LLEC or LLEF system can be removed from a garment for the ability and replaced with a new system as needed.

Certain embodiments are designed for universal conformability with any area of the body, for example a flat area or a contoured area. In embodiments the dressings are configured to conform to the area to be treated, for example by producing the dressing in particular shapes including "slits" or discontinuous regions. In embodiments the dressing can be produced in a U shape wherein the "arms" of the U are substantially equal in length as compared to the "base" of the U. In embodiments the dressing can be produced in a U shape wherein the "arms" of the U are substantially longer in length as compared to the "base" of the U. In embodiments the dressing can be produced in a U shape wherein the "arms" of the U are substantially shorter in length as compared to the "base" of the U. In embodiments the dressing can be produced in an X shape wherein the "arms" of the X are substantially equal in length. In embodiments the universal dressing can be used to treat, for example, muscles, or skin, for example to treat "road rash."

The systems and devices can comprise corresponding or interlocking perimeter areas to assist the devices in maintaining their position on the patient and/or their position relative to each other. In certain embodiments, the systems and devices can comprise a port or ports to provide access to the treatment area beneath the device.

LLEC/LLEF Systems, Devices, and Methods of Use

Embodiments disclosed herein include LLEC and LLEF systems that can promote and/or accelerate the muscle recovery process and optimize muscle performance. For example, muscles work when calcium ions are released, which trigger muscle cells to contract. Proteins called actin and myosin form filaments, which form cross-bridges during contraction. The actin and myosin filaments pull past each other when a flood of calcium ions signals contraction, and this causes the muscle sheath to become shorter. This leads all the sheaths (called "sarcomeres") to shorten, and the contraction is synchronized across the entire muscle. The contracting muscles pull on tendons, which in turn pull on the bones to which they are attached. All muscle contractions are triggered by electrical impulses which travel from the brain to the nerve endings in contact with the actin and myosin filaments. Embodiments disclosed herein can increase intracellular calcium levels by exposing cells to the electric field produced by disclosed embodiments.

Further, embodiments disclosed herein can direct cell migration.

Further embodiments can increase cellular protein sulfhydryl levels and cellular glucose uptake. Increased glucose uptake can result in greater mitochondrial activity and thus increased glucose utilization.

Disclosed methods of use comprise application of a system or device described herein to a tissue, for example a joint or muscle or muscle group. In embodiments, the application can be performed prior to, during, or after use of the muscle or muscle group to be treated. For example, a shoulder can be treated prior to engaging in an athletic activity, for example pitching a baseball.

Disclosed embodiments can prevent or limit muscle injury, for example by activating enzymes that aid in the muscle recovery process, increasing glucose uptake, driving redox signaling, increasing $H_2O_2$ production, increasing cellular protein sulfhydryl levels, and increasing (IGF)-1 R phosphorylation.

Disclosed embodiments can repair muscle damage (for example such as can occur during a workout), for example by activating enzymes that aid in the muscle recovery process, increasing glucose uptake, driving redox signaling, increasing $H_2O_2$ production, increasing cellular protein sulfhydryl levels, and increasing (IGF)-1 R phosphorylation.

Disclosed embodiments can improve muscle recovery, for example by activating enzymes that aid in the muscle recovery process, increasing glucose uptake, driving redox signaling, increasing $H_2O_2$ production, increasing cellular protein sulfhydryl levels, and increasing (IGF)-1 R phosphorylation.

Disclosed embodiments can improve muscle function, for example by activating enzymes, increasing glucose uptake, driving redox signaling, increasing $H_2O_2$ production, increasing cellular protein sulfhydryl levels, and increasing (IGF)-1 R phosphorylation.

Disclosed embodiments can improve athletic performance, for example by activating enzymes, increasing glucose uptake, driving redox signaling, increasing $H_2O_2$ production, increasing cellular protein sulfhydryl levels, and increasing (IGF)-1 R phosphorylation.

Disclosed embodiments can produce an electrical stimulus and/or can electro-motivate, electro-conduct, electro-induct, electro-transport, and/or electrophorese one or more therapeutic materials in areas of target tissue (e.g., iontophoresis), and/or can cause one or more biologic or other materials in proximity to, on or within target tissue to be rejuvenated. Further disclosure relating to materials that can produce an electrical stimulus can be found in U.S. Pat. No. 7,662,176 entitled FOOTWEAR APPARATUS AND METHODS OF MANUFACTURE AND USE issued Feb. 16, 2010, which is incorporated herein by reference in its entirety.

Methods disclosed herein can include applying a disclosed embodiment to an area to be treated. Embodiments can include selecting or identifying a patient in need of treatment. In embodiments, methods disclosed herein can include application of a device disclosed herein to an area to be treated.

In embodiments, disclosed methods include application to the treatment area or the device of an antibacterial. In embodiments the antibacterial can be, for example, alcohols, aldehydes, halogen-releasing compounds, peroxides, anilides, biguanides, bisphenols, halophenols, heavy metals, phenols and cresols, quaternary ammonium compounds, and the like. In embodiments the antibacterial agent can comprise, for example, ethanol, isopropanol, glutaraldehyde, formaldehyde, chlorine compounds, iodine compounds, hydrogen peroxide, ozone, peracetic acid, formaldehyde, ethylene oxide, triclocarban, chlorhexidine, alexidine, polymeric biguanides, triclosan, hexachlorophene, PCMX (p-chloro-m-xylenol), silver compounds, mercury compounds, phenol, cresol, cetrimide, benzalkonium chloride, cetylpyridinium chloride, ceftolozane/tazobactam, ceftazidime/avibactam, ceftaroline/avibactam, imipenem/MK-7655, plazomicin, eravacycline, brilacidin, and the like.

In embodiments, compounds that modify resistance to common antibacterials can be employed. For example, some resistance-modifying agents may inhibit multidrug resistance mechanisms, such as drug efflux from the cell, thus increasing the susceptibility of bacteria to an antibacterial. In embodiments, these compounds can include Phe-Arg-β-naphthylamide, or β-lactamase inhibitors such as clavulanic acid and sulbactam.

In embodiments, the system can also be used for preventative treatment of tissue injuries. Preventative treatment can include preventing the reoccurrence of previous muscle injuries. For example, a garment can be shaped to fit a patient's shoulder to prevent recurrence of a deltoid injury.

EXAMPLES

The following non-limiting examples are provided for illustrative purposes only in order to facilitate a more complete understanding of representative embodiments. These examples should not be construed to limit any of the embodiments described in the present specification.

Example 1

Cell Migration Assay

The in vitro scratch assay is a well-developed method to measure cell migration in vitro. The basic steps involve creating a "scratch" in a cell monolayer, capturing images at the beginning and at regular intervals during cell migration to close the scratch, and comparing the images to quantify the migration rate of the cells. Compared to other methods, the in vitro scratch assay is particularly suitable for studies on the effects of cell-matrix and cell-cell interactions on cell migration, mimic cell migration during wound healing in vivo and are compatible with imaging of live cells during migration to monitor intracellular events if desired. In addition to monitoring migration of homogenous cell populations, this method has also been adopted to measure migration of individual cells in the leading edge of the scratch.

Human keratinocytes were plated under plated under placebo or a LLEC system as described herein (labeled "PROCELLERA®"). Cells were also plated under silver-only or zinc-only dressings. After 24 hours, the scratch assay was performed. Cells plated under the PROCELLERA® device displayed increased migration into the "scratched" area as compared to any of the zinc, silver, or placebo dressings. After 9 hours, the cells plated under the PROCELLERA® device had almost "closed" the scratch. This demonstrates the importance of electrical activity to cell migration and infiltration.

In addition to the scratch test, genetic expression was tested. Increased insulin growth factor (IGF)-1 R phosphorylation was demonstrated by the cells plated under the PROCELLERA® device as compared to cells plated under insulin growth factor alone.

Integrin accumulation also affects cell migration. An increase in integrin accumulation was achieved with the LLEC system. Integrin is necessary for cell migration, and is found on the leading edge of migrating cell.

Thus, the tested LLEC system enhanced cellular migration and IGF-1 R/integrin involvement. This involvement demonstrates the effect that the LLEC system had upon cell receptors involved with the wound healing process.

Example 2

Wound Care Study

The medical histories of patients who received "standard-of-care" wound treatment ("SOC"; n=20), or treatment with a LLEC device as disclosed herein (n=18), were reviewed. The wound care device used in the present study consisted of a discrete matrix of silver and zinc dots. A sustained voltage of approximately 0.8 V was generated between the dots. The electric field generated at the device surface was measured to be 0.2-1.0 V, 10-50 µA.

Wounds were assessed until closed or healed. The number of days to wound closure and the rate of wound volume reduction were compared. Patients treated with LLEC received one application of the device each week, or more frequently in the presence of excessive wound exudate, in conjunction with appropriate wound care management. The LLEC was kept moist by saturating with normal saline or conductive hydrogel. Adjunctive therapies (such as negative pressure wound therapy [NPWT], etc.) were administered with SOC or with the use of LLEC unless contraindicated. The SOC group received the standard of care appropriate to the wound, for example antimicrobial dressings, barrier creams, alginates, silver dressings, absorptive foam dressings, hydrogel, enzymatic debridement ointment, NPWT, etc. Etiology-specific care was administered on a case-by-case basis. Dressings were applied at weekly intervals or more. The SOC and LLEC groups did not differ significantly in gender, age, wound types or the length, width, and area of their wounds.

Wound dimensions were recorded at the beginning of the treatment, as well as interim and final patient visits. Wound dimensions, including length (L), width (W) and depth (D) were measured, with depth measured at the deepest point. Wound closure progression was also documented through digital photography. Determining the area of the wound was performed using the length and width measurements of the wound surface area.

Closure was defined as 100% epithelialization with visible effacement of the wound. Wounds were assessed 1 week post-closure to ensure continued progress toward healing during its maturation and remodeling phase.

Wound types included in this study were diverse in etiology and dimensions, thus the time to heal for wounds was distributed over a wide range (9-124 days for SOC, and 3-44 days for the LLEC group). Additionally, the patients often had multiple co-morbidities, including diabetes, renal disease, and hypertension. The average number of days to wound closure was 36.25 (SD=28.89) for the SOC group and 19.78 (SD=14.45) for the LLEC group, p=0.036. On average, the wounds in the LLEC treatment group attained closure 45.43% earlier than those in the SOC group.

Based on the volume calculated, some wounds improved persistently while others first increased in size before improving. The SOC and the LLEC groups were compared to each other in terms of the number of instances when the dimensions of the patient wounds increased (i.e., wound treatment outcome degraded). In the SOC group, 10 wounds (50% for n=20) became larger during at least one measurement interval, whereas 3 wounds (16.7% for n=18) became larger in the LLEC group (p=0.018). Overall, wounds in both groups responded positively. Response to treatment was observed to be slower during the initial phase, but was observed to improve as time progressed.

The LLEC wound treatment group demonstrated on average a 45.4% faster closure rate as compared to the SOC group. Wounds receiving SOC were more likely to follow a "waxing-and-waning" progression in wound closure compared to wounds in the LLEC treatment group.

Compared to localized SOC treatments for wounds, the LLEC (1) reduces wound closure time, (2) has a steeper wound closure trajectory, and (3) has a more robust wound healing trend with fewer incidence of increased wound dimensions during the course of healing.

Example 3

LLEC Influence on Human Keratinocyte Migration

An LLEC-generated electrical field was mapped, leading to the observation that LLEC generates hydrogen peroxide, known to drive redox signaling. LLEC-induced phosphorylation of redox-sensitive IGF-1 R was directly implicated in cell migration. The LLEC also increased keratinocyte mitochondrial membrane potential.

The LLEC was made of polyester printed with dissimilar elemental metals as described herein. It comprises alternating circular regions of silver and zinc dots, along with a proprietary, biocompatible binder added to lock the electrodes to the surface of a flexible substrate in a pattern of discrete reservoirs. When the LLEC contacts an aqueous solution, the silver positive electrode (cathode) is reduced while the zinc negative electrode (anode) is oxidized. The LLEC used herein consisted of metals placed in proximity of about 1 mm to each other thus forming a redox couple and generating an ideal potential on the order of 1 Volt. The calculated values of the electric field from the LLEC were consistent with the magnitudes that are typically applied (1-10 V/cm) in classical electrotaxis experiments, suggesting that cell migration observed with the bioelectric dressing is likely due to electrotaxis.

Measurement of the potential difference between adjacent zinc and silver dots when the LLEC is in contact with de-ionized water yielded a value of about 0.2 Volts. Though the potential difference between zinc and silver dots can be measured, non-intrusive measurement of the electric field arising from contact between the LLEC and liquid medium was difficult. Keratinocyte migration was accelerated by exposure to an Ag/Zn LLEC. Replacing the Ag/Zn redox couple with Ag or Zn alone did not reproduce the effect of keratinocyte acceleration.

Exposing keratinocytes to an LLEC for 24 h significantly increased green fluorescence in the dichlorofluorescein (DCF) assay indicating generation of reactive oxygen species under the effect of the LLEC. To determine whether $H_2O_2$ is generated specifically, keratinocytes were cultured with a LLEC or placebo for 24 h and then loaded with PF6-AM (Peroxyfluor-6 acetoxymethyl ester; an indicator of endogenous $H_2O_2$). Greater intracellular fluorescence was observed in the LLEC keratinocytes compared to the cells grown with placebo. Over-expression of catalase (an enzyme that breaks down $H_2O_2$) attenuated the increased migration triggered by the LLEC. Treating keratinocytes with N-Acetyl Cysteine (which blocks oxidant-induced signaling) also failed to reproduce the increased migration observed with LLEC. Thus, $H_2O_2$ signaling mediated the increase of keratinocyte migration under the effect of the electrical stimulus.

External electrical stimulus can up-regulate the TCA (tricarboxylic acid) cycle. The stimulated TCA cycle is then expected to generate more NADH and $FADH_2$ to enter into the electron transport chain and elevate the mitochondrial membrane potential (Am). Fluorescent dyes JC-1 and TMRM were used to measure mitochondrial membrane potential. JC-1 is a lipophilic dye which produces a red fluorescence with high Am and green fluorescence when Am is low. TMRM produces a red fluorescence proportional to Am. Treatment of keratinocytes with LLEC for 24 h demonstrated significantly high red fluorescence with both JC-1 and TMRM, indicating an increase in mitochondrial membrane potential and energized mitochondria under the effect of the LLEC. As a potential consequence of a stimulated TCA cycle, available pyruvate (the primary substrate for the TCA cycle) is depleted resulting in an enhanced rate of glycolysis. This can lead to an increase in glucose uptake in order to push the glycolytic pathway forward. The rate of glucose uptake in HaCaT cells treated with LLEC was examined next. More than two fold enhancement of basal glucose uptake was observed after treatment with LLEC for 24 h as compared to placebo control.

Keratinocyte migration is known to involve phosphorylation of a number of receptor tyrosine kinases (RTKs). To determine which RTKs are activated as a result of LLEC, scratch assay was performed on keratinocytes treated with LLEC or placebo for 24 h. Samples were collected after 3 h and an antibody array that allows simultaneous assessment of the phosphorylation status of 42 RTKs was used to quantify RTK phosphorylation. It was determined that LLEC significantly induces IGF-1 R phosphorylation. Sandwich ELISA using an antibody against phospho-IGF-1 R and total IGF-1 R verified this determination. As observed with the RTK array screening, potent induction in phosphorylation of IGF-1 R was observed 3 h post scratch under the influence of LLEC. IGF-1 R inhibitor attenuated the increased keratinocyte migration observed with LLEC treatment.

MBB (monobromobimane) alkylates thiol groups, displacing the bromine and adding a fluoresce nt tag (lamda emission=478 nm). MCB (monochlorobimane) reacts with only low molecular weight thiols such as glutathione. Fluorescence emission from UV laser-excited keratinocytes loaded with either MBB or MCB was determined for 30 min. Mean fluorescence collected from 10,000 cells showed a significant shift of MBB fluorescence emission from cells. No significant change in MCB fluorescence was observed, indicating a change in total protein thiol but not glutathione. HaCaT cells were treated with LLEC for 24 h followed by a scratch assay. Integrin expression was observed by immuno-cytochemistry at different time points. Higher integrin expression was observed 6 h post scratch at the migrating edge.

Consistent with evidence that cell migration requires $H_2O_2$ sensing, we determined that by blocking $H_2O_2$ signaling by decomposition of $H_2O_2$ by catalase or ROS scavenger, N-acetyl cysteine, the increase in LLEC-driven cell migration is prevented. The observation that the LLEC increases $H_2O_2$ production is significant because in addition to cell migration, hydrogen peroxide generated in the wound margin tissue is required to recruit neutrophils and other leukocytes to the wound, regulates monocyte function, and VEGF signaling pathway and tissue vascularization. Therefore, external electrical stimulation can be used as an effective strategy to deliver low levels of hydrogen peroxide over time to mimic the environment of the healing wound and thus should help improve wound outcomes. Another phenomenon observed during re-epithelialization is increased expression of the integrin subunit alpha-v. There is evidence that integrin, a major extracellular matrix receptor, polarizes in response to applied ES and thus controls directional cell migration. It may be noted that there are a number of integrin subunits, however we chose integrin aV because of evidence of association of alpha-v integrin with IGF-1 R, modulation of IGF-1 receptor signaling, and of driving keratinocyte locomotion. Additionally, integrin alpha v has been reported to contain vicinal thiols that provide site for redox activation of function of these integrins and therefore the increase in protein thiols that we observe under the effect of ES may be the driving force behind increased integrin mediated cell migration. Other possible integrins which may be playing a role in LLEC-induced IGF-1 R mediated keratinocyte migration are a5 integrin and a6 integrin.

Materials and Methods

Cell culture—Immortalized HaCaT human keratinocytes were grown in Dulbecco's low-glucose modified Eagle's medium (Life Technologies, Gaithersburg, Md., U.S.A.)

supplemented with 10% fetal bovine serum, 100 U/ml penicillin, and 100 µg/ml streptomycin. The cells were maintained in a standard culture incubator with humidified air containing 5% C02 at 37° C.

Scratch assay—A cell migration assay was performed using culture inserts (IBIDI®, Verona, Wis.) according to the manufacturers instructions. Cell migration was measured using time-lapse phase-contrast microscopy following withdrawal of the insert. Images were analyzed using the AxioVision Rel 4.8 software.

N-Acetyl Cysteine Treatment—Cells were pretreated with 5 mM of the thiol antioxidant N-acetylcysteine (Sigma) for 1 h before start of the scratch assay.

IGF-1 R inhibition—When applicable, cells were preincubated with 50 nM IGF-1 R inhibitor, picropodophyllin (Calbiochem, Mass.) just prior to the Scratch Assay.

Cellular $H_2O_2$ Analysis—To determine intracellular $H_2O_2$ levels, HaCaT cells were incubated with 5 pM PF6-AM in PBS for 20 min at room temperature. After loading, cells were washed twice to remove excess dye and visualized using a Zeiss Axiovert 200M microscope.

Catalase gene delivery—HaCaT cells were transfected with $2.3 \times 10^7$ pfu AdCatalase or with the empty vector as control in 750 µl of media. Subsequently, 750 µl of additional media was added 4 h later and the cells were incubated for 72 h.

RTK Phosphorylation Assay—Human Phospho-Receptor Tyrosine Kinase phosphorylation was measured using Phospho-RTK Array kit (R & D Systems).

ELISA—Phosphorylated and total IGF-1 R were measured using a DuoSet IC ELISA kit from R&D Systems.

Determination of Mitochondrial Membrane Potential—Mitochondrial membrane potential was measured in HaCaT cells exposed to the LLEC or placebo using TMRM or JC-1 (MitoProbe JC-1 Assay Kit for Flow Cytometry, Life Technologies), per manufacturers instructions for flow cytometry.

Integrin alpha V Expression—Human HaCaT cells were grown under the MCD or placebo and harvested 6 h after removing the IBIDI® insert. Staining was done using antibody against integrin aV (Abeam, Cambridge, Mass.).

Example 4

Generation of Superoxide

A LLEC system was tested to determine the effects on superoxide levels which can activate signal pathways. PROCELLERA® LLEC system increased cellular protein sulfhydryl levels. Further, the PROCELLERA® system increased cellular glucose uptake in human keratinocytes. Increased glucose uptake can result in greater mitochondrial activity and thus increased glucose utilization, providing more energy for cellular migration and proliferation. This can "prime" the wound healing process before a surgical incision is made and thus speed incision healing.

Example 5

Effect on *Propionibacterium acnes*

Bacterial Strains and Culture

The main bacterial strain used in this study is *Propionibacterium acnes* and multiple antibiotics-resistant *P. acnes* isolates are to be evaluated.

ATCC medium (7 *Actinomyces* broth) (BD) and/or ATCC medium (593 chopped meat medium) is used for culturing *P. acnes* under an anaerobic condition at 37° C. All experiments are performed under anaerobic conditions.

Culture

LNA (Leeming-Notman agar) medium is prepared and cultured at 34° C. for 14 days.

Planktonic Cells

*P. acnes* is a relatively slow-growing, typically aerotolerant anaerobic, Gram-positive bacterium (rod). *P. acnes* is cultured under anaerobic condition to determine for efficacy of an embodiment disclosed herein (PROCELLERA®). Overnight bacterial cultures are diluted with fresh culture medium supplemented with 0.1% sodium thioglycolate in PBS to $10^5$ colony forming units (CFUs). Next, the bacterial suspensions (0.5 mL of about 105) are applied directly on PROCELLERA® (2"×2") and control fabrics in Petri-dishes under anaerobic conditions. After 0 h and 24 h post treatments at 37° C., portions of the sample fabrics are placed into anaerobic diluents and vigorously shaken by vortexing for 2 min. The suspensions are diluted serially and plated onto anaerobic plates under an anaerobic condition. After 24 h incubation, the surviving colonies are counted. The LLEC limits bacterial proliferation.

Example 6

Pre-Treatment and Post-Treatment of Surgical Procedures

Prior to surgery the patient wears a LLEC compression garment over the surgical site, such as the upper arm or bicep area. Surgical procedures can include procedures used to treat tenotomy, biceps tendonitis, or rotator cuff injury. The compression garment consists of an integrated layer of standard PROCELLERA®. Prior to applying the compression garment an activating agent can be applied. A compression sleeve or shirt provides an intimate contact between the electrodes and the skin with minimal movement.

The LLEC compression garment with integrated PROCELLERA® can be worn for 24 hours prior to surgery to initiate incision-healing process by; 1) reducing or eliminating microorganism presence around the incision site; 2) increasing integrin accumulation; 3) increasing cellular protein sulfhydryl levels; 4) increasing $H_2O_2$ production; and 5) up-regulating the TCA (tricarboxylic acid) cycle.

The same LLEC compression garment and method can also be applied to a patient's surgical site post-surgery for accelerated healing or treatment.

Example 7

Availability of Cellular Energy and Lactate Threshold

The lactate threshold, also known as lactate inflection point or anaerobic threshold, is the exercise intensity at which lactate (more specifically, lactic acid) starts to accumulate in the blood stream. The reason for the acidification of the blood at high exercise intensities is two-fold: the high rates of ATP hydrolysis in the muscle release hydrogen ions, as they are co-transported out of the muscle into the blood via the monocarboxylate transporter, and also bicarbonate stores in the blood begin to be used up. This happens when lactate is produced faster than it can be removed (metabolized) in the muscle. When exercising at or below the lactate threshold, lactate produced by the muscles is removed by the body without it building up (e.g., aerobic respiration). When exercising at or above the lactate threshold (e.g. anaerobic respiration), excess lactate can build up in tissue causing a lower pH and soreness, called acidosis. This excess lactate build-up decreases athletic ability during exercise as well tissue recovery after exercise and can be a primary source of post-exercise muscle stiffness/pain.

Prior to exercise or activity the patient wears a LLEC compression garment over his body, such as the upper body using a shirt, the lower body using pants, or a combination of both. The compression garment consists of an integrated layer of standard PROCELLERA® The PROCELLERA® can be configured to penetrate into superficial muscle tissue under the compression garment. The PROCELLERA® system increased cellular glucose uptake. Increased glucose uptake can result in greater mitochondrial activity and thus increased glucose utilization, providing more energy for cellular activity to remove lactic acid from muscle tissue. It has been shown that increased cellular glucose utilization can also sustain anaerobic respiration for a longer period of time during exercise, thus increasing a person's lactate threshold. An increased lactate threshold prevents lactate from building-up in muscle tissue, thus reducing or preventing muscle damage and/or pain.

Example 8

Use in Muscle Damage Prevention

During exercise or activity the patient wears a LLEC compression garment over his body, such as the upper body using a shirt, the lower body using shorts, or a combination of both. The compression garment consists of an integrated layer of standard PROCELLERA® as disclosed herein. The PROCELLERA® can be configured to penetrate into muscle tissue under the compression garment. The PROCELLERA® system increases cellular glucose uptake. Increased glucose uptake can result in greater mitochondrial activity and thus increased glucose utilization, aiding in muscle damage prevention.

Example 9

Use in Muscle Recovery

After exercise or activity the patient wears a LLEC compression garment over his body, such as the upper body using a shirt, the lower body using shorts, or a combination of both. The compression garment consists of an integrated layer of standard PROCELLERA® as disclosed herein. The PROCELLERA® can be configured to penetrate into muscle tissue under the compression garment. The PROCELLERA® system increases cellular glucose uptake. Increased glucose uptake can result in greater mitochondrial activity and thus increased glucose utilization, aiding in muscle recovery.

Example 10

Availability of Cellular Energy and Lactate Threshold

During exercise or activity the patient wears a LLEC compression garment over his body, such as the upper body using a shirt, the lower body using pants, or a combination of both. The compression garment consists of an integrated layer of standard PROCELLERA® The PROCELLERA® can be configured to penetrate into superficial muscle tissue under the compression garment. The PROCELLERA® system increased cellular glucose uptake. Increased glucose uptake can result in greater mitochondrial activity and thus increased glucose utilization, providing more energy for cellular activity to remove lactic acid from muscle tissue. It has been shown that an increased cellular glucose utilization can also sustain anaerobic respiration for a longer period of time during exercise, thus increasing a person's lactate threshold. An increased lactate threshold prevents lactate from building-up in muscle tissue, thus reducing or preventing muscle damage and/or pain.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, including the best mode known to the inventor for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A stretchable quadriceps injury treatment device, comprising:
    a garment adapted to fit a leg of a subject, said garment comprising a substrate wherein the garment substrate comprises a compression fabric, wherein said compression fabric exerts a pressure of between 40 mmHg and 50 mmHg on the quadriceps and a lesser pressure on the subject's lower leg; and
    a plurality of biocompatible electrodes configured to generate at least one of a low level electric field (LLEF) or low level electric current (LLEC), wherein the biocompatible electrodes comprise a first array comprising a first pattern of microcells formed from a first conductive material, and a second array comprising a second pattern of microcells formed from a second conductive material, wherein the diameter of each microcell in the first array is 1.5 mm+/−1 mm and the diameter of each microcell in the second array is 2.5 mm+/−2 mm, and the first and second conductive materials comprise different materials.

2. The device of claim 1 wherein the first array and the second array spontaneously generate the LLEF.

3. The device of claim 2 wherein the first array and the second array spontaneously generate the LLEC when contacted with an electrolytic solution.

4. A method for treating a quadricep injury, comprising:
    Applying to the quadriceps a stretchable garment adapted to fit a leg of a subject, said garment comprising a substrate comprising a compression fabric comprising a plurality of biocompatible electrodes, wherein said compression fabric exerts a pressure of between 40 mmHg and 50 mmHg on the quadriceps and a lesser pressure on the subject's lower leg, wherein said plurality of biocompatible electrodes comprises:
        a first array comprising a pattern of microcells comprising a first conductive material; and
        a second array comprising a pattern of microcells comprising a second conductive material, such arrays capable of defining at least one voltaic cell for spontaneously generating at least one electrical current with the conductive material of the first array when said first and second arrays are introduced to an electrolytic solution, wherein the diameter of each microcell is in the first array is 1.5 mm+/−1 mm and the diameter of each microcell in the second array is 2.5 mm+/−2 mm and the first and second conductive materials comprise different materials;
    wherein the garment substrate provides a low level electric current (LLEC) of between 1 and 200 micro-amperes to the quadriceps for muscle recovery.

5. The method of claim 4, wherein said treating muscle comprises increasing cellular protein sulfhydryl levels.

6. The method of claim 4, wherein said treating muscle comprises increasing cellular glucose uptake to provide an increased availability of cellular energy.

7. A method for preventing quadriceps injury, comprising:
    Applying to the quadriceps a stretchable garment adapted to fit a leg of a subject, said garment comprising a substrate comprising a compression fabric comprising a plurality of biocompatible electrodes, wherein said compression fabric exerts a pressure of between 40 mmHg and 50 mmHg on the quadriceps and a lesser pressure on the subject's lower leg; wherein said plurality of biocompatible electrodes comprises:
        a first array comprising a pattern of microcells comprising a first conductive material; and
        a second array comprising a pattern of microcells comprising a second conductive material, such arrays capable of defining at least one voltaic cell for spontaneously generating at least one electrical current with the conductive material of the first array when said first and second arrays are introduced to an electrolytic solution, wherein the diameter of each microcell is in the first array is 1.5 mm+/−1 mm and the diameter of each microcell in the second array is 2.5 mm+/−2 mm and the first and second conductive materials comprise different materials;
    wherein the garment substrate provides a low level microcurrent (LLEC) of between 1 and 200 micro-amperes to the quadriceps.

* * * * *